United States Patent [19]
Demassey et al.

[11] Patent Number: 6,159,973
[45] Date of Patent: Dec. 12, 2000

[54] AROMATIC AMIDES, THEIR PREPARATION PROCESS, THE COMPOSITIONS CONTAINING THEM AND THEIR USE AS PESTICIDES

[75] Inventors: Jacques Demassey, Montevrain; Michel Gohar, Rousset; Christian Wehrey, Villemomble, all of France

[73] Assignee: Hoechst Schering Agrevo S.A., France

[21] Appl. No.: 09/358,623

[22] Filed: Jul. 21, 1999

Related U.S. Application Data

[62] Division of application No. 08/894,068, filed as application No. PCT/FR96/00123, Jul. 25, 1996, Pat. No. 6,013,837.

[30] Foreign Application Priority Data

Jan. 26, 1995 [FR] France ..................... 95 00889

[51] Int. Cl.⁷ ............ A01N 43/84; C07D 295/13; C07D 295/192
[52] U.S. Cl. ............ 514/237.8; 544/58.4; 544/169; 544/176; 546/226; 546/309; 548/195; 548/246; 548/251; 548/539; 548/550; 548/567; 548/950; 548/966; 549/77; 549/419; 549/493
[58] Field of Search .................. 544/169, 176; 548/567; 514/237.8

[56] References Cited

U.S. PATENT DOCUMENTS 4,962,107 10/1990 Nakamura et al. .............. 544/176

*Primary Examiner*—Robert W. Ramsuer
*Attorney, Agent, or Firm*—Bierman, Muserlian and Lucas

[57] ABSTRACT

The subject of the invention is the compounds of formula (I):

$$Q(CH_2)_a-(X_1)_b-Q_1-Q_2-C(X_2)-N(R_1)(R_2) \quad (I)$$

in which:
Q represents an aryl radical,
$X_1$ represents oxy, thio, sulphinyl or sulphonyl,
$X_2$ represents oxygen or sulphur,
$Q_1$ represents a cyclopropanediyl radical,
$Q_2$ represents an arylene radical,
$R_1$ and $R_2$ represent:
either a hydrogen atom or a hydrocarbon radical
or one of the groups $$R_3-C=X_3, (R_3)_2-P=X_3, T_2-R_5 \text{ or } S(O)_j-N(R_6)(R_7)$$

in which $X_3$ represents an oxygen atom or a sulphur atom, $T_2$ represents a bivalent oxy, carbonyl or oxycarbonyl group and j is equal to 0, 1 or 2,
their preparation process and their use as pesticides.

13 Claims, No Drawings

AROMATIC AMIDES, THEIR PREPARATION PROCESS, THE COMPOSITIONS CONTAINING THEM AND THEIR USE AS PESTICIDES

PRIOR APPLICATIONS

This application is a division of U.S. patent application Ser. No. 894,068 filed Jul. 30, 1997, now U.S. Pat. No. 6,013,537 which is a 371 application of PCT/FR96/00123 filed Jul. 25, 1996.

The present invention relates to new aromatic amides, their preparation process, the compositions containing them and their use as pesticides.

Certain 5-cyclopropyl pentadieneamides are described in the European Patent Applications published under the numbers 0,369,762, 0,524,041 and 0,553,081 as having such properties.

It has now been found that the compounds corresponding to formula (I) as defined hereafter also have useful pesticide properties, which make them capable of being used for the protection of plants, safeguarding hygiene in public or private premises, as well as for the implementation of therapeutic treatment for veterinary use, or even for human use.

The products of formula (I) are moreover photostable and not very toxic for mammals and therefore correspond perfectly to the requirements of the modern agrochemical industry.

Therefore a subject of the present invention is in all their stereoisomeric forms or in the form of stereoisomer mixtures, the compounds of formula (I):

$$Q(CH_2)_a - (X_1)_b - Q_1 - Q_2 - C(X_2) - N(R_1)(R_2) \quad (I)$$

in which:

Q represents an aryl radical or a radical derived from a condensed bicyclic hydrocarbon containing a benzene ring, which is linked to an adjacent $(CH_2)_a$ group by a carbon atom of said benzene ring, Q contains 6 to 12 carbon atoms and can be either non-substituted or substituted, a and b are identical or different and independently of each other are equal to 0 or to 1, $X_1$ represents a bivalent oxy, thio, sulphinyl or sulphonyl radical, $X_2$ represents an oxygen atom or a sulphur atom, $Q_1$ represents a cyclopropanediyl radical, which is either non-substituted or substituted, $Q_2$ represents an arylene radical or a radical derived from a condensed bicyclic hydrocarbon containing a benzene ring, which is linked to the adjacent $Q_1$ and $C(X_2)$ groups by two carbon atoms of said benzene ring, $Q_2$ contains 6 to 12 carbon atoms and can independently of Q, be either non-substituted or substituted, $R_1$ and $R_2$ represent independently of each other:

either a hydrogen atom, or a radical derived from a saturated or unsaturated, linear or branched, aromatic or non-aromatic, cyclic or acyclic hydrocarbon, and containing 1 to 12 carbon atoms, itself being able to be either non-substituted or substituted, or a radical derived from a linear or branched structure containing 1 to 20 carbon atoms and 1 to 6 heteroatoms chosen from oxygen, nitrogen or sulphur atoms, itself being able to be either non-substituted or substituted, or a radical derived from an aromatic or non-aromatic heterocycle containing 5 to 9 carbon atoms and 1 to 4 heteroatoms chosen from oxygen, nitrogen or sulphur atoms, this radical being able to be non-substituted or substituted, or a group (A):

$$R_3 - \overset{\overset{\displaystyle X_3}{\|}}{C} -$$

in which $X_3$ represents an oxygen atom or a sulphur atom, and $R_3$ represents a hydrogen atom or an $R_4-(T_1)_i$ group in which i is equal to 0 or to 1, $T_1$ represents a bivalent oxy, carbonyl or oxycarbonyl group and $R_4$ represents a hydrogen atom or a radical derived from a saturated or unsaturated, linear or branched, aromatic or non-aromatic, cyclic or acyclic hydrocarbon, and containing 1 to 20 carbon atoms, itself being able to be either non-substituted or substituted, or a group (B):

$$(R_3)_2 - \overset{\overset{\displaystyle X_3}{\|}}{P} -$$

in which $R_3$ and $X_3$ are as defined above,
or a group (C):

$$-T_2-R_5$$

in which $T_2$ represents a bivalent thio, sulphinyl, sulphonyl or sulphonyloxy radical and $R_5$ represents an hydrogen atom or a radical derived from a saturated or unsaturated, linear or branched, aromatic or non-aromatic, cyclic or acyclic hydrocarbon, and containing 1 to 8 carbon atoms, itself being able to be either non-substituted or substituted, or a group (D):

$$[S(O)_j]_k - N(R_6)(R_7)$$

in which j is equal to 0, 1 or 2, k is equal to 0 or 1, $R_6$ represents a hydrogen atom or a radical derived from a saturated or unsaturated, linear or branched, aromatic or non-aromatic, cyclic or acyclic hydrocarbon, and containing 1 to 8 carbon atoms, itself being able to be either non-substituted or substituted, and $R_7$ represents a carboxy, fluorocarbonyl, alkoxycarbonyl group containing 2 to 5 carbon atoms, or an acyl radical containing 1 to 5 carbon atoms, or an alkyl radical containing 1 to 4 carbon atoms substituted by a cyano group or by an alkoxycarbonyl radical containing 2 to 5 carbon atoms, or an acyl radical containing 1 to 5 carbon atoms, or by an aryl radical containing 6 to 10 carbon atoms, non-substituted or substituted by one or more groups chosen from halo, cyano, nitro, trifluoromethyl, trifluoromethoxy, trifluoromethylthio groups or alkyl radicals containing 1 to 4 carbon atoms or alkoxy radicals containing 1 to 4 carbon atoms or $R_6$ and $R_7$ form together with the nitrogen atom to which they are linked a nitrogenous heterocycle containing 3 to 10 members containing optionally one or more cyclic heteroatoms chosen among oxygen, nitrogen or sulphur and optionally substituted, or $R_1$ and $R_2$ represent together with the nitrogen atom to which they are linked a nitrogenous heterocycle containing 3 to 10 members containing optionally one or more cyclic heteroatoms chosen among oxygen, nitrogen or sulphur and optionally substituted, it being understood that in said formula (I) when Q represents a 2-(phenylamino-carbonyl) phenyl radical, $Q_1$ a 1,2-cyclopropanediyl radical, $Q_2$ an ortho-phenylene radical, $X_2$ an oxygen atom, $R_2$ a hydrogen atom and a and b are equal to 0, $R_1$ does not represent a phenyl radical.

By compound of formula (I) is designated all the possible geometric isomers and stereoisomers taken individually or in a mixture.

By radical derived from a condensed bicyclic hydrocarbon containing a benzene ring, is designated in particular for the definition of Q the indanyl, indenyl, dihydronaphthyl or tetrahydronaphthyl radicals and for the definition of $Q_2$ in particular the following radicals: ortho-phenylene, meta-phenylene, para-phenylene, 1,2-naphthylene, 1,3-naphthylene, 1,4-naphthylene, 4,5-indenylene, 4,6-indenylene, 4,7-indenylene, 4,5-indanylene, 4,6-indanylene, 4,7-indanylene, 1,2,3,4-tetrahydro 5,6-naphthylene, 1,2,3,4-tetrahydro 5,7-naphthylene, 5,8-tetrahydronaphthylene.

By radical derived from a saturated or unsaturated, aromatic or non-aromatic, cyclic hydrocarbon, is designated in particular the phenyl radical, cycloalkyl radicals such as cyclopropyl, cyclobutyl, cyclopentyl or cyclohexyl radicals as well as alkyl radicals substituted by a cyclic radical such as the benzyl or cyclopropylmethyl radical.

By radical derived from a saturated or unsaturated, linear or branched, acyclic hydrocarbon, is designated alkyl radicals such as in particular methyl, ethyl, propyl, isopropyl, butyl, isobutyl, sec-butyl, tert-butyl, pentyl, isopentyl, neopentyl, tert-pentyl, hexyl or isohexyl, alkenyl radicals, such as in particular vinyl, 1-propenyl, 2-methyl 2-propenyl, isopropenyl radicals, alkynyl radicals such as in particular ethynyl, 1-propynyl, 2-propynyl radicals as well as radicals containing several unsaturations such as alkadienyl radicals such as 1,3-butadienyl or pent-2-ene-4-ynyl radical.

By radical derived from a linear or branched structure, containing 1 to 20 carbon atoms and 1 to 6 heteroatoms, is designated in particular the radicals derived from alkanes some of the carbon atoms of which are replaced by oxygen, sulphur atoms or an —NH— group, such as the following radicals: hydroxymethyl, methoxymethyl, ethoxymethyl, 2-hydroxyethyl, 2-methoxyethyl, 2-(2-methoxy ethoxy) ethyl, (2-methoxyethoxy) methyl, [2-(2-methoxy ethoxy) ethoxy] methyl, ethoxymethyl, [2-(2-butoxy ethoxy) ethoxy] methyl, 2-methylthio ethyl, 2-(methylamino) ethyl, methylaminomethyl, butylaminobutyl or propoxymethyl.

By radical derived from an aromatic or non-aromatic heterocycle, is designated in particular the following radicals: thienyl, furyl, pyrannyl, pyrrolyl, 2H-pyrrolyl, imidazolyl, pyrazolyl, pyridyl, pyrazinyl, pyrimidinyl, pyridazinyl, isothiazolyl, isoxazolyl, furazannyl, thiazolyl, oxazolyl, pyrrolidinyl, pyrrolinyl, imidazolidinyl, pyrazolinyl, piperidyl, piperazinyl, morpholinyl, azepinyl, thiazinyl, tetrazinyl, oxathiolannyl or thiadiazinyl.

When Q is substituted by one or more substituants, these substituents are chosen in particular from halogen atoms or the following groups: methylenedioxy, difluoromethylenedioxy, tetrafluoro ethylenedioxy, cyano, nitro, cyanato, thiocyanato, pentafluorothio, fluorosulphonyl or R—(T)$_c$— in which R represents a hydrogen atom or a radical derived from a saturated or unsaturated, linear or branched, aromatic or non-aromatic, cyclic or acyclic hydrocarbon and containing 1 to 8 carbon atoms, itself being able to be either non-substituted or substituted by one or more halogen atoms, c is equal to 0 or 1 and T represents a bivalent oxy, carbonyl, carbonyloxy, oxycarbonyl, thio, sulphinyl, sulphonyl, or sulphonyloxy group, a —(CO)$_d$—N(R')—(CO)$_e$—(O)$_f$— or —N(R")—S(O)$_g$— group in which R' and R" represent independently of R a hydrogen atom, or a radical derived from a saturated or unsaturated, linear or branched, aromatic or non-aromatic, cyclic or acyclic hydrocarbon and containing 1 to 8 carbon atoms, itself being able to be either non-substituted or substituted by one or more halogen atoms, d, e and f are equal to 0 or 1, f is equal to 0 when e is equal to 0, the sum of e+d is equal to 0 or 1, and g is equal 0, 1 or 2.

When $Q_1$ is substituted, the substituents are chosen in particular from halogen atoms, cyano, azido radicals, or saturated or unsaturated, aliphatic radicals containing 1 to 4 carbon atoms non-substituted or substituted by one or more halogen atoms, such as methyl, vinyl or ethynyl radicals.

When $Q_2$ is substituted, these substituents are chosen in particular from halogen atoms or methylenedioxy, difluoromethylenedioxy, tetrafluoro ethylenedioxy, cyano, nitro, amino, alkylamino, alkenylamino, cyanato, thiocyanato, pentafluorothio, fluorosulphonyl groups or an R—(T)$_c$— group in which R represents a hydrogen atom or a radical derived from a saturated or unsaturated, linear or branched, aromatic or non-aromatic, cyclic or acyclic hydrocarbon and containing 1 to 8 carbon atoms, itself being able to be either non-substituted or substituted by one or more halogen atoms, c is equal to 0 or 1 and T represents a bivalent oxy, carbonyl, carbonyloxy, oxycarbonyl, thio, sulphinyl, sulphonyl, or sulphonyloxy group, a —(CO)$_d$—N(R')—(CO)$_e$—(O)$_f$— or —N(R")—S(O)$_g$— group in which R', R", d, e, f and g are as defined previously.

When in what precedes or in what follows, it is indicated that a radical can be substituted by one or more halogen atoms, these halogen atoms can be fluorine, chlorine, bromine or iodine atoms. When it is a radical poly-substituted by fluorine atoms, the perfluorinated radicals are in particular designated.

When in what precedes, a radical derived from a saturated or unsaturated, linear or branched, aromatic or non-aromatic, cyclic or acyclic hydrocarbon is substituted, these substituents are chosen in particular from halogen atoms or the methylenedioxy, difluoromethylenedioxy, tetrafluoro ethylenedioxy, cyano, nitro, cyanato, thiocyanato, pentafluorothio, fluorosulphonyl groups or an R—(T)$_c$— group in which R represents a hydrogen atom or a radical derived from a saturated or unsaturated, linear or branched, aromatic or non-aromatic, cyclic or acyclic hydrocarbon and containing 1 to 8 carbon atoms and optionally one or more heteroatoms, itself being able to be either non substituted or substituted by one or more halogen atoms, c is equal 0 or to 1 and T represents a bivalent oxy, carbonyl, carbonyloxy, oxycarbonyl, thio, sulphinyl, sulphonyl, or sulphonyloxy group, a —(CO)$_d$—N(R')—(CO)$_e$—(O)$_f$— or —N(R")—S(O)$_g$— group in which R', R", d, e, f and g are as defined previously.

The compounds of formula (I) in which Q, $Q_1$, $Q_2$ are non-substituted or substituted as described in the preceding paragraphs, constitute a first preferred variant of the present invention.

In a second preferred variant of the present invention, Q represents a phenyl radical or a naphthyl radical, non substituted or substituted by 1 to 3 substituents and in particular a radical chosen from the following radicals: phenyl, 2-chloro phenyl, 3-chloro phenyl, 3-bromophenyl, 3-(trifluoromethyl) phenyl, 4-chloro phenyl, 4-bromo phenyl, 4-iodo phenyl, 4-(trifluoromethyl) phenyl, 4-nitrophenyl, 4-methoxy phenyl, 4-(difluoromethoxy) phenyl, 4-(trifluoromethoxy) phenyl, 3-bromo 4-(difluoromethoxy) phenyl, 4-(2,2-dibromo ethenyl) phenyl, 4-ethynyl phenyl, 4-benzyl phenyl, 3,4-dibromo phenyl, 2,4-dichlorophenyl, 3,4-dichloro phenyl, 3,4-difluorophenyl, 3-chloro 4-iodo phenyl, 4-bromo 3-chloro phenyl, 4-bromo 2-fluoro phenyl, 4-bromo 3-fluoro phenyl, 4-bromo 3-(trifluoromethyl) phenyl, 4-chloro 3-(trifluoromethyl) phenyl, 3,5-bis-(trifluoromethyl) phenyl, 3,4,5-trichloro phenyl, 4-bromo 3,5-dichloro phenyl, 3-phenoxy-phenyl, 4-(fluoro 3-phenoxy) phenyl, 3-bromo 4-(trifluoro-methylsulphonyloxy) phenyl, 3,4-bis (trifluoromethyl-sulphonyloxy) phenyl, 2-naphthyl or 5-bromo 2-naphthyl or 6-bromo 1-napthyl.

In a third preferred variant of the present invention, the steric configuration of $Q_1$ is such that the Q—$(CH_2)_a$—$(X_1)_b$— group is in trans position relative to the $Q_2$—$C(X_2)$—$N(R_1)(R_2)$ group.

In a fourth preferred variant of the present invention, $Q_1$ is non-substituted or substituted by 1 or 2 halogen atoms or by 1 or 2 methyl radicals and in particular a radical chosen from the following radicals: 1,2-cyclopropanediyl, 1-fluoro 1,2-cyclopropanediyl, 1-chloro 1,2-cyclopropanediyl, 1-bromo 1,2-cyclopropanediyl, 1-methyl 1,2-cyclopropanediyl, 3,3-dibromo 1,2-cyclopropanediyl and 1,2-difluoro 1,2-cyclopropanediyl.

In a fifth preferred variant of the present invention, $Q_2$ represents one of the following radicals: ortho-phenylene, meta-phenylene, para-phenylene, 1,2-naphthylene, 1,3-naphthylene, 1,4-naphthylene, 1,5-naphthylene, 2,5-naphthylene, 4,5-indenylene, 4,6-indenylene, 4,7-indenylene, 4,5-indanylene, 4,6-indanylene, 4,7-indanylene, 1,2,3,4-tetrahydro 5,6-naphthylene, 1,2,3,4-tetrahydro 5,7-naphthylene, 1,2,3,4-tetrahydro 5,8-naphthylene, non-substituted or substituted by 1 to 4 substituants, and in particular the following radicals: 2-methyl 1,4-phenylene, 2,3,5,6-tetrafluoro 1,4-phenylene, 3-methyl 1,4-phenylene, 2-chloro 1,4-phenylene, 2-acetylamino 5-chloro 1,4-phenylene, 2-amino 5-chloro 1,4-phenylene, 2-dimethylamino 5-chloro 1,4-phenylene.

In a sixth preferred variant of the present invention, $R_1$ represents a branched alkyl radical containing 1 to 6 carbon atoms such as one of the following radicals: isopropyl, isobutyl, 1,2-dimethyl propyl, 1,1,2-trimethyl propyl ou 2,2-dimethyl propyl, 1-methylpropyl, 2-methylbutyl, 2,2-dimethyl 1-methylethyl, 3-chloropropyl, cyclobutyl, cyclohexyl, cyclopropylmethyl, a (2-methyl 1,3-dioxolan 2-yl) methyl radical, or a branched alkenyl radical containing 2 to 5 carbon atoms such as the 2-methyl 2-propenyl, 2-chloro 2-propenyl, 2-bromo 2-propenyl radical or also a non-substituted phenyl radical or a substituted phenyl radical such as one of the following radicals: 2-fluoro phenyl, 2-chloro phenyl, 2-bromo phenyl, 2-iodo phenyl, 2-nitro phenyl, 2-hydroxy phenyl, 2-methoxyphenyl, 2-cyano phenyl, 2-amino phenyl, 2-(dimethylamino) phenyl, 2-(trifluoromethoxy) phenyl, 2-phenoxy phenyl, 2-methoxycarbonyl phenyl, 2-ethoxy-carbonyl phenyl, 2-phenylcarbonylphenyl, 2-formyl phenyl, 2-acetyl phenyl, 2-(methylthio) phenyl, 2-fluorosulphonyl phenyl, 2-ethynyl phenyl, 2-(1-methyl 2-propenyl) phenyl, 2-(hydroxymethyl) phenyl, 2-methyl phenyl, 2-(terbutyl) phenyl, 2-(fluoromethyl) phenyl, 2-(difluoromethyl) phenyl, 2-(trifluoromethyl) phenyl, 2-ethyl phenyl, 2-propyl phenyl, 2-isopropyl phenyl, 2-(pyridin-1-yl) phenyl, 3-chloro phenyl, 3-bromo phenyl, 3-methoxy phenyl, 3-fluoro phenyl, 3-methyl phenyl, 3-phenoxy phenyl, 4-fluoro phenyl, 4-chloro phenyl, 4-cyano phenyl, 4-(cyanomethyl) phenyl, 4-methoxy phenyl, 4-methyl phenyl, 4-(terbutyl) phenyl), 4-(trifluoromethyl) phenyl, 4-phenoxyphenyl, 4-benzyloxyphenyl, 4-methoxy-carbonylphenyl, 4-cyclohexylphenyl, 2,4-dichlorophenyl, 2,5-dichlorophenyl, 2,6-dichlorophenyl, 3,4-dichlorophenyl, 3,5-dichlorophenyl, 2,3-dimethylphenyl, 2,4-dimethylphenyl, 2,5-dimethylphenyl, 2,6-dimethylphenyl, 3,5-dimethylphenyl, 2,4,6-trimethylphenyl, 2,5-dimethoxyphenyl, 3,4-dimethoxyphenyl, 3,5-dimethoxyphenyl, 2-methoxy 5-methylphenyl, 2-methoxy 5-trifluoromethyl, 3-methoxy 5-trifluoromethylphenyl, 2-methoxy 5-nitrophenyl, 2-nitro 4-methoxyphenyl, 2-methyl 4-methoxyphenyl, 3,5-dichloro 4-methoxyphenyl, 4,5-dichloro 2-methoxyphenyl, 4-bromo 3,5-dichlorophenyl, 2-(1-methylethyl) phenyl, 3-chloro 2-methyl phenyl, 3-fluoro 2-methyl phenyl, 3-bromo 2-methyl phenyl, 2,3-dichloro phenyl, 2,3-dibromo phenyl, 3,4-dibromo phenyl, 4-fluoro 2-methyl phenyl, 4-chloro 2-fluoro phenyl, 4-fluoro 2-(trifluoromethyl) phenyl, 2,4-difluoro phenyl, 2-chloro 4-methylphenyl, 2-chloro 5-methyl phenyl, 5-chloro 2-methyl phenyl, 5-fluoro 2-methyl phenyl, 5-iodo 2-methyl phenyl, 2,6-difluoro phenyl, 2-fluoro 4-methyl phenyl, 2-fluoro 6-methyl phenyl, 2-chloro 6-methyl phenyl or a radical derived from a heterocycle such as the 2-chloro 3-pyridyl, 3-pyridyl, 2-pyridyl, 4-pyridyl, 2-chloro 3-pyridyl, 3-methyl pyridyl, 5-methyl isoxazol-3-yl, 1,3,4-thiadiazol-2-yl, 4-pyrimidinyl, 3-pyrazolyl, 4-(trifluoromethyl) thiazol-2-yl, 5-chloro 4-(trifluoromethyl) thiazol-2-yl, 1-piperidinyl, 2,6-dimethyl 1-piperidinyl, 1,4-oxazin-4-yl or 1-perhydroazepinyl radical, or finally $R_1$ et $R_2$ represent together with the nitrogen atom to which they are linked a heterocycle such as the 1,4-thiazin-4-yl, 1,4-oxazin-4-yl, 1-aziridinyl, 1-piperidinyl, 1-pyrrolidinyl, 2-methylpiperidin-1-yl, 2-hydroxymethyl-pyrrolidin-1-yl radical.

In a seventh preferred variant of the present invention, $R_2$ represents a hydrogen atom, an alkyl radical containing 1 to 4 carbon atoms, in particular the ethyl radical, a benzyl radical, an ethoxymethyl radical, a propoxymethyl radical, a group (A) in which $X_3$ represents an oxygen atom and $R_3$ represents an alkyl radical containing 1 to 11 carbon atoms, an alkoxycarbonyl radical containing 2 to 5 carbon atoms or a phenoxycarbonyl radical, and $R_2$ represents in particular in this case, the acetyl hexanoyl, decanoyl, 2-methoxy 2-oxo acetyl, 2-ethoxy 2-oxo acetyl, or 2-phenoxy 2-oxo acetyl radical, a group (B) in which $R_3$ represents an alkoxy radical containing 1 to 4 carbon atoms and $R_2$ represents in particular in this case the diethoxyphosphonyl radical, a group (C) in which $T_2$ represents a bivalent thio radical and $R_5$ a trifluoromethyl or pentafluoroethyl radical or a phenyl radical non substituted or substituted by one or more halogen atoms or by one or more alkyl radicals containing 1 to 4 carbon atoms, and in this case $R_2$ represents in particular the trifluoromethylthio, pentafluoroethylthio, or phenylthio, (4-chloro phenyl) thio, (2-methyl phenyl) thio, (4-methyl phenyl) thio or (4-tertbutyl phenyl) thio radical or a group (D) in which j is equal to O and $R_2$ represents in particular in this case the (N-formyl N-methyl amino) thio or (N-methoxycarbonyl N-methyl amino) thio radical.

In an eighth preferred variant, a and b are equal to 0.

In particular a subject of the invention is the compounds whose names follow:

-4-(1-fluoro 2-phenyl cyclopropyl) N-isobutyl benzenamide (cis+trans isomers, cis/trans=3/2)

-4-(1-fluoro 2-phenyl cyclopropyl) N-(2-methyl phenyl) benzenamide (cis+trans isomers, cis/trans=3/1)

-4-[2-(4-chloro phenyl) cyclopropyl] N-isobutyl benzenamide (trans isomer)

-4-[2-(4-chloro phenyl) 1-fluoro cyclopropyl] N-ethyl N-(2-methyl phenyl) benzenamide (cis isomer)

-4-[2-(3,4-dibromo phenyl) 1-fluoro cyclopropyl] N-(2-methyl phenyl) benzenamide (cis isomer)

-4-[2-(3,4-dibromo phenyl) 1-fluoro cyclopropyl] N-isobutyl benzenamide (cis isomer)

-4-[2-(4-chloro phenyl) 1-fluoro cyclopropyl] N-isobutyl benzenamide (cis isomer)

-4-[2-(4-chloro phenyl) 1-fluoro cyclopropyl] N-(2-methyl phenyl) benzenamide (cis isomer)

-4-[2-(4-chloro phenyl) 1-fluoro cyclopropyl] N-isobutyl benzenamide (trans isomer)

-4-[2-(4-chloro phenyl) 1-fluoro cyclopropyl] N-(2-methyl phenyl) benzenamide (trans isomer)

-4-[2-(3,4-dichloro phenyl) 1-fluoro cyclopropyl] N-(2-methyl phenyl) benzenamide (cis isomer)

-4-[2-(3,4-dichloro phenyl) 1-fluoro cyclopropyl] N-ethyl N-(2-methyl phenyl) benzenamide (cis isomer)

-4-[2-(3,4,5-trichloro phenyl) 1-fluoro cyclopropyl] N-(2-methyl phenyl) benzenamide (cis isomer)

-4-[2-(3,4-dibromo phenyl) 1-fluoro cyclopropyl] N-methyl N-(2-methyl phenyl) benzenamide (cis isomer)

-4-[2-(4-trifluoromethoxy phenyl) 1-fluoro cyclopropyl] N-(2-methyl phenyl) benzenamide (cis isomer)

-4-[2-(3,4-dibromo phenyl) 1-fluoro cyclopropyl] N-(2,6-dimethyl phenyl) benzenamide (cis isomer)

-4-[2-(3,4-dibromo phenyl) 1-fluoro cyclopropyl] N-(2,4,6-trimethyl phenyl) benzenamide (cis isomer)

-4-[2-(3,4-dichloro phenyl) 1-fluoro cyclopropyl] N-[2-(fluoromethyl) phenyl] benzenamide (cis isomer)

-4-[2-(3,4-dibromo phenyl) 1-fluoro cyclopropyl] N-(2-methyl phenyl) benzene thioamide (cis isomer)

-4-[2-(3,4-dibromo phenyl) 1-fluoro cyclopropyl] N-ethyl N-(2-methyl phenyl) benzene thioamide (cis isomer)

-4-[2-(3,4-dibromo phenyl) 1-fluoro cyclopropyl] N-(1,4-oxazin-4-yl) benzenamide (cis isomer).

Also a subject of the invention is a preparation process for the compounds of formula (I), characterized in that the acid or corresponding acid derivative of formula (II):

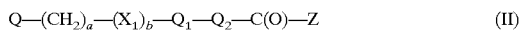

in which Q, a, b, $Q_1$ and $Q_2$ are as defined previously and Z represents a hydroxy group, a halogenated group, an alkoxy radical containing 1 to 4 carbon atoms or a —P(O)(Oo)—NHo group, in which o represents a phenyl group, is reacted with an amine of formula (III):

in which $R_1$ and $R_2$ are as defined previously, in order to obtain a corresponding product of formula (I), in which $X_2$ represents an oxygen atom, which if necessary, is converted into a product of formula (I) in which ($X_2$) represents a sulphur atom.

The products of formula (I) obtained according to the above process can be, if appropriate, separated into their optically-active isomers.

The separation of the isomers can be carried out according to methods known to a man skilled in the art for example by photochemical, thermic or chromatographic route.

According to the preferred conditions for implementing the preparation process for the compounds of formula (I) as indicated above, the amidification reaction is in general carried out at a temperature comprised between –25 and +150° C. in an anhydrous and aprotic solvent such as ether, dichloro-methane, toluene or benzene.

The precise reaction conditions also depend on the nature of the Z group; for example when Z represents an alkoxy group, the reaction is carried out at a high temperature for example between 250 and 125° C., in particular 50° C. and preferably in the presence of a trialkylaluminium, such as trimethylaluminium, which forms a complex with the amine of formula (III).

When Z represents a halogenated group, or phosphoroimidate, the reaction is carried out between 0° and 30° C., in particular at an ordinary temperature and preferably in the presence of a tertiary amine, such as triethylamine. The conversion of an amide into thioamide takes place according to methods known to a man skilled in the art, such as reaction of the amide with phosphorus pentasulphide, hydrogen sulphide, boron trisulphide or thiophosphoryl bromide.

When the derivative of the acid of formula (II) is an acid halide, for example the acid chloride, it is prepared from the acid by reaction with the appropriate reagent such as oxalyl chloride or thionyl chloride. When Z represents a —P(O)(Oo)—NHo group, the corresponding derivative is prepared from the acid by reaction with Cl—P(O)(Oo)—NHo. The acid of formula (II) in which Z represents a hydroxy group can be prepared by hydrolyzing an ester.

The preparation of the compound of formula (II) in which Z represents an alkoxy radical can be carried out in particular:

a) by cyclopropanation of a compound of formula (IV):

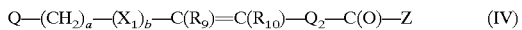

in which Q, a, $X_1$, b, $Q_2$ and Z are as defined previously and $R_9$ and $R_{10}$ represent, independently of each other, a hydrogen atom, a halogen atom or an alkyl radical, with a carbene generator, such as diazomethane, dibromomethane or diiodo-methane in the presence of diethylzinc;

b) by cyclocondensation of a derivative of formula (V):

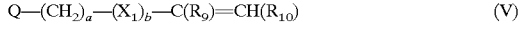

in which Q, a, $X_1$, b, $R_9$ and $R_{10}$ are as defined previously with a compound of formula (VI):

to lead to the compound of formula (II) in which $Q_1$ represents a cyclopropanediyl radical substituted in position 1 by a fluorine atom.

The acid of formula (II) in which Z represents a hydroxy radical can also be prepared by elimination of nitrogen from a compound of formula (VII):

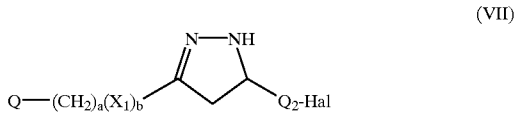

to lead to the compound of formula (VIII):

in which Q, a, $X_1$, b, $Q_2$ are as defined previously, Hal represents a bromine or iodine atom and $Q_1$ represents a non-substituted cyclopropanediyl radical, which product of formula (VIII) is transformed into a cyano derivative of formula (IX):

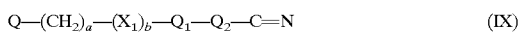

which is then converted into the corresponding acid of formula (II).

The compound of formula (VII) is prepared by reaction of hydrazine with the compound of formula (X):

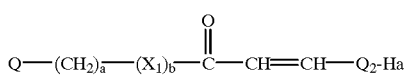 (X)

the compound of formula (X) is prepared by condensation in a basic medium of a compound of formula (XI):

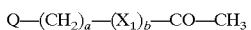 (XI)

with an aromatic aldehyde of formula (XII):

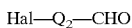 (XII)

which products of formulae (XI) and (XII) are either commercially-available or easily synthesizable by a man skilled in the art.

The compound of formula (VI) is prepared by bromination of a compound of formula (XIII):

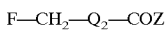 (XIII)

which itself is prepared from a compound of formula (XIV):

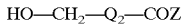 (XIV)

which is commercially-available or easily synthesizable by a man skilled in the art.

The compounds of formulae (IV) and (V) are known or can be obtained according to the usual methods known to a man skilled in the art.

The experimental conditions are illustrated by the examples described in the present Application.

Also a subject of the invention is the compounds of formulae (II), (VI), (VII), (VIII), (IX) and (X) with the exception of-the products whose names follow:

methyl 5-(2-phenyl cyclopropyl) 2-acetoxy benzoate
methyl 2-(2-phenyl cyclopropyl) benzoate
1,2-diphenyl cyclopropane 4,4'di carbonitrile
4-[2-(1-naphthyl) cyclopropyl] benzonitrile and
3-(4-bromo phenyl) 1-phenyl propenone and with the exception of the products of formula (VIII) in which $X_1$ represents a sulphonyl group.

The compounds of formula (I) can be used for combating harmful organisms such as arthropods, for example insects and acarids, and helminths, for example nematodes, or molluscs, for example slugs. Therefore a subject of the present invention is a process for combating arthropods and/or helminths and/or molluscs, which includes the administration to arthropods and/or helminths and/or molluscs or to their environment of a sufficient quantity of a compound of formula (I) to destroy the harmful organism. A subject of the present invention is also a process for combating and/or eradicating infestations by arthropods and/or helminths and/or molluscs in animals (including human beings) and/or plants (including trees) and/or stored products, which includes the administration to the animal or site of an effective quantity of a compound of formula (I). A subject of the invention is also the compounds of formula (I) for use in human and veterinary medicine, in public health and/or in agriculture to combat harmful arthropods and/or helminths.

The compounds of formula (I) are particularly valuable for the protection of standing crops, fodder plants, plantations, greenhouse crops, orchards and vineyards, ornamental plants and trees in plantations and in forests, for example cereals (such as corn, wheat, rice and sorghum), cotton, tobacco, legumes and salad plants (such as beans, cabbages, curcubitacae, lettuces, onions, tomatoes and sweet peppers), food crops (for example potatoes, sugar beet, groundnuts, soya and rape), sugar cane, grasslands and fodder crops (such as corn, sorghum and alfalfa), plantations (such as those producing tea, coffee, cocoa, bananas, palm oil, coconuts, rubber and spices), orchards and planted woods (such as those producing stone fruits and pomaceous fruits, citrus fruits, kiwis, avocadoes, mangoes, olives and nuts), vines, ornamental plants, flowers and bushes grown in greenhouses and in gardens and parks, forest trees (both deciduous and evergreen) in forests, plantations and nurseries.

They are also invaluable for the protection of timber (standing, felled, processed, stored or in building) against attack by sirex (for example Urocerus), coleoptera (for example scolytidae, platypodidae, lyctidae, bostrychidae, cerambucidae and anobiidae) and termites.

They are used for the protection of stored products, such as grains, fruits, nuts, spices and tobacco, in the whole state, powdered or converted into products, against attack by mites, coleoptera and weevils. They also protect stored animal products, such as skins, furs, wool and feathers, in a natural or converted form (for example as carpets or textile materials), against attack by mites and coleoptera, as well as for meat and fish against attack by coleoptera and flies.

The compounds of general formula (I) are of particular use for combating the arthropods, helminths or molluscs which are harmful to man and domestic animals or are propagators or vectors of illnesses affecting the latter, for example those described above, more especially in the area of combating ticks, mites, lice, fleas, midges and flies, which cause bites and are a nuisance.

In particular the invention relates to the use of the the compounds of formula (I) as defined previously, as a pesticide in particular as insecticides, acaricides and nematicides in the protection of crops, in particular rice and cotton crops, or for the treatment of premises for storing products of said crops and in particular as an insecticide or acaricide in domestic or public premises.

The compounds of formula (I) can be used to such ends by the use of the compounds as they are or in diluted form in a known manner as a bath, spray, drift, varnish, foam, powder, dusting powder, aqueous suspension, paste, gel, shampoo, ointment, combustible solid, vaporization mat, combustible coil, bait, food supplement, wettable powder, granules, aerosol, emulsifiable concentrates, oily suspensions, oily solutions, pressurized spray, impregnated article, lotion or other standard compositions well known to a man skilled in the art. The bath concentrates are not used as they are, but diluted with water and the animals are immersed in a tank containing the bath. The sprays can be applied by hand or using a spraying lance or spraying boom. The animal, the soil, the plant or the surface can be saturated with the spray by application in high volume or be superficially covered with the spray by the application of a small or ultrasmall volume. The aqueous suspensions can be applied to the animal in the same way as the sprays and the baths. The dusting powders can be distributed by means of a powder applicator or, in the case of animals, be incorporated in perforated bags attached to trees or to poles. The pastes, shampoos and ointments can be applied by hand or distributed over the surface of an inert material against which the animals rub themselves and thus transfer the material onto their skin. The lotions are distributed in the form of a small volume dose of liquid on the back of the animals, so that all or the majority of the liquid remains on the animals.

The compounds of formula (I) can be presented as compositions which are ready to use on plants, animals and surfaces or as compositions which have to be diluted before use, but the compositions of both types contain a compound of formula (I) in an intimate mixture with one or more excipients or diluting agents. The excipients can be liquid, solid or gaseous or can contain mixtures of such substances and the compound of formula (I) can be present at a concentration of 99 to 0.025% w/v, depending on whether the composition must be more or less diluted.

The dusting powders, powders and granules contain the compound of formula (I) in an intimate mixture with a pulverulent inert solid excipient, for example appropriate clays, kaolin, bentonite, attapulgite, adsorbant carbon black, talc, mica, chalk, gypsum, tricalcium phosphate, powdered cork, magnesium silicate, plant excipients, starch and diatomaceous earth. These solid compositions are generally prepared by impregnating the solid diluting agents with solutions of the compound of formula (I) in volatile solvents, by evaporatng the solvents and, if desired, by grinding up the products in order to obtain powders and, if desired, by granulating, by pressing or by encapsulating the products.

The sprays of a compound of formula (I) can contain a solution in an organic solvent (for example those set out below) or an emulsion in water (bath or shower) prepared on site from an emulsifiable concentrate (also called oil miscible in water), which can also serve for the immersion. The concentrate preferably contains a mixture of the active constituent, with or without an organic solvent and one or more emulsifying agents. The solvents can be present within wide limits, but preferably in a quantity of 0 to 90% w/v of the composition and can be chosen from kerosene, ketones, alcohols, xylene, aromatic naphtha and other known solvents for use in compositions. The concentration of emulsifying agents can vary within wide limits, but is preferably situated within the range 5 to 25% w/v and the emulsifying agents are advantageously non-ionic surfactants, in particular polyoxy-alkylenic esters of alkylphenols and polyoxyethylenic derivatives of hexitol anhydrides, or anionic surfactants, in particular sodium laurylsulphate, ether sulphates of fatty alcohols, sodium and calcium salts of alkylarylsulphonates and alkylsulphosuccinates.

The cationic emulsifying agents are in particular benzalkonium chloride and quaternary ammonium ethosulphates.

The amphoteric emulsifying agents are in particular carboxymethylated oleic imidazoline and the alkyl dimethylbetaines.

The vaporisation mats normally contain a mixture of cotton and cellulose pressed into a plate of about 32 mm by 22 mm by 3 mm treated with a quantity of up to 0.3 ml of a concentrate which contains the active constituent in an organic solvent and optionally an anti-oxidant, a colouring agent and a perfume.

The insecticide is vaporized by a heat source, such as an electrical heating apparatus for mats.

The combustible solids normally contain sawdust and a binding agent in a mixture with the active ingredient and shaped into strips (normally as a coil). A colouring agent and a fungicide can also be added.

The wettable powders contain an inert solid excipient, one or more surfactants and optionally stabilizing agents and/or anti-oxidants.

The emulsifiable concentrates contain emulsifying agents and often an organic solvent such as kerosene, ketones, alcohols, xylenes, aromatic naphtha and other known solvents.

The wettable powders and emulsifiable concentrates normally contain 5 to 95% by weight of the active ingredient and are diluted before use, for example with water.

The varnishes contain a solution of the active ingredient in an organic solvent, together with a resin and optionally a plasticizer.

The baths can be prepared not only from emulsifiable concentrates, but also from wettable powders, baths based on soap and aqueous suspensions containing a compound of formula (I) in an intimate mixture with a dispersing agent and one or more surfactants.

The aqueous suspensions of a compound of formula (I) can contain a suspension in water together with a suspension agent, stabilizers or other agent. The suspensions or solutions can be used as they are or in a form diluted in a known manner.

The ointments (or greases) can be prepared from vegetable oils, synthetic esters of fatty acids or lanoline, together with an inert base such as soft paraffin. A compound of formula (I) is preferably evenly distributed in the mixture in solution or suspension. The ointments can also be obtained from emulsifiable concentrates by dilution of the latter in an ointment base.

The pastes and shampoos are also semi-solid compositions in which a compound of formula (I) can be present as a uniform dispersion in an appropriate base, such as liquid or soft paraffin, or in a non-fatty base with glycerol, glue or a suitable soap. Due to the fact that the ointments, shampoos and pastes are usually applied without further dilution, they must contain the appropriate percentage of the compound of formula (I) required for the treatment.

The aerosol sprays can be prepared as a simple solution of the active ingredient in the aerosol propellant and a cosolvant such as a halogenated alkane and the solvents mentioned above, respectively. The lotion compositions can be presented as a solution or suspension of a compound of formula (I) in a liquid medium. A bird or mammal host can also be protected against infestation by ectoparasitic acarids by carrying a manufactured product fashioned in a suitably moulded plastic material which is impregnated with a compound of formula (I). These manufactured products include collars, ear tags, bands, cloths and strips suitably attached on the appropriate part of the body. The plastic material is advantageously a poly (vinyl chloride).

Therefore a particular subject of the invention is a composition containing:
a) a compound of formula (I) as defined previously,
b) inert excipients suitable for the use as pesticides of said product of formula (I),
a composition containing:
a) a compound of formula (I) as defined previously,
b) inert excipients suitable for the use in veterinary field of said product of formula (I),
and a compound of formula (I) as defined previously, for the implementation of a treatment method for the human or animal body characterized in that a pharmaceutically acceptable formulation of said compound is applied to said body.

The compounds of formula (I) are for use in the protection and the treatment of plant species, in which case an effective insecticide, acaricide, molluscide, nematocide quantity of the active ingredient is applied. The applied dose varies according to the compound chosen, the nature of the composition, the application method, the type of plant, the density of planting, the probable infestation and various other factors, but in general a dose suitable for agriculture is situated in the range 0.001 to 3 kg per hectare and preferably between 0.01 and 1 kg per hectare. The typical compositions for agricultural use contain between 0.0001% and 50% of a compound of formula (I) and advantageously between 0.1 and 15% by weight of a compound of formula (I).

The concentration of the compound of formula (I) for use on an animal, premises or outside locations varies according to the compound chosen, the interval between treatments, the nature of the composition and the probable infestation, but in general the compound must be contained in the composition applied in a quantity of 0.001 to 20.0% w/v, preferably 0.01 to 10% w/v. The quantity of the compound deposited on an animal varies according to the application method, the size of the animal, the concentration of the compound in the composition applied, the dilution factor of the composition and the nature of the composition, but is generally situated in the range 0.0001% to 0.5% w/w, except for the non-diluted compositions, such as the lotion compositions which are generally deposited at a concentration in the range 0.1 to 20.0% and preferably 0.1 to 10%. The quantity of compound to be applied to stored products is generally situates in the range 0.1 to 20 ppm. Sprayings in opens spaces can be carried out so as to produce an average initial concentration of 0.001 to 1 mg of the compound of formula (I) per $m^3$ of treated area.

The ointments, greases, pastes and aerosols are usually applied randomly as described above and concentrations of 0.001 to 20% w/v of a compound of formula (I) in the applied composition can be used.

The compounds of formula (I) have been shown to have an activity against the house-fly (Musca domestica). In addition, some compounds of formula (I) have an activity against other harmful arthropods, in particular *Myzus persicae, Tetranychus urticae, Spodoptera littoralis, Heliotuis virescens, Plutella xylostella,* Culex spp., *Tribolium castaneum, Sitophilus-granarius, Periplaneta americana* and *Blattella germanica.* The compounds of formula (I) are therefore useful for combating arthropods, for example insects and acarids, in any environment where they constitute a nuisance, for example in agriculture, in breeding, in public health and in the domestic environment.

The harmful insects are in particular members of the orders of coleoptera (for example Anobium, Ceuthorrhynchus, Rhynchophorus, Cosmopolites, Lissorhoptrus, Meligethes, Hypothenemus, Hylesinus, Acalymma, Lema, Psylliodes, Leptinotarsa, Gonocephalum, Agriotes, Dermolepida, Heteronychus, Phaedon, Tribolium, Sitophilus, Diabrotica, Anthonomus or Anthrenus spp.), lepidoptera (for example Ephestia, Mamestra, Earias, Pectinophora, Ostrinia, Trichloplusia, Pieris, Laphygma, Agrotis, Amathes, Wiseana, Tryporyza, Diatraea, Sparganothis, Cydia, Archips, Plutella, Chilo, Heliothis, *Spodoptera littoralis, Helrotuis virescens,* Spodoptera or Tineola spp.), diptera (for example Musca, Aedes, Anopheles, Culex, Glossina, Simulium, Stomoxys, Haematobia, Tabanus, Hydrotaea, Lucilia, Chrysomyia, Callitroga, Dermatobia, Gasterophilus, Hypoderma, Hylemyia, Atherigona, Chlorops, Phytomyza, Ceratitis, Liriomyza and Melophagus spp.), phthiraptera (Mallophaga, for example Damalina spp., and Anoplura, for example Linognathus and Haematopinus spp.), hemiptera (for example Aphis, Bemisia, Phorodon, Aeneolamia, Empoasca, Parkinsiella, Pyrilla, Aonidiella, Coccus, Pseudococcus, Helopeltis, Lygus, Dysdercus, Oxycarenus, Nezara, Aleyrodes, Triatoma, Psylla, Myzus, Megoura, Phylloxera, Adelges, Nilaparvata, Nephotettix or Cimwx spp.), orthoptera (for example Locusta, Gryllus, Schistocerca or Acheta spp.), dictyoptera (for example Blattella, Periplaneta or Blatta spp.), hymenoptera (for example Athalia, Cephus, Atta, Solenopsis or Monomorium spp.); isoptera (for example Odontotermes and Reticulitermes spp.), siphonaptera (for example Ctenocephalides or Pulex spp.), thysanura (for example Lepisma spp.), dermaptera (for example Forficula spp.) and psocoptera (for example Peripsocus spp.) and thysanoptera (for example *Thrips tabaci*).

The harmful acarids are notably ticks, for example members of genus Boophilus, Ornithodorus, Rhipicephalus, Amblyomma, Hyalomma, Ixodes, Haemaphysalis, Dermacentor and Anocentor, and mites and scabies mites such as Acarus, Tetranychus, Psoroptes, Notoednes, Sarcoptes, Psorergates, Chorioptes, Eutrombicula, Demodex, Panonychus, Bryobia, Eriophyes, Blaniulus, Polyphagotarsonemus, Scutigerella and Oniscus spp.

The nematodes which attack plants and trees which are important in agriculture, forestry and horticulture, both directly and by propagating bacterial, viral, mycoplasmic or fungal diseases of plants, are in particular the root scab nematodes, such as Meloidogyne spp. (for example *M. incognita*); the nematodes of roots, such as Globodera spp. (for example *G. rostochiensis*); Heterodera spp. (for example *H. avenae*); Radopholus spp. (for example *R. similis*); the nematodes of grasslands, such as Pratylenchus spp. (for example *P. pratensis*); Belonolaimus spp (for example *B. gracilis*); Tylenchulus spp. (for example *T. semipenetrans*); Rotylenchulus spp. (for example *R. reniformis*); Rotylenchus spp. (for example *R. robustus*); Helicotylenchus spp. (for example *H. multicinctus*); Hemicycliophora spp. (for example *H. gracilis*); Criconemoides spp. (for example *C. similis*); Trichodorus spp. (for example *T. primitivus*); the xiphophore nematodes, such as Xiphinema spp. (for example *X. diversicaudatum*), Longidorus spp. (for example *L. elongatus*); Hoplolaimus spp. (for example *H. coronatus*); Aphelenchoides spp. (for example *A. ritzemabosi, A. besseyi*); and the nematodes of bulbs, such as Ditylenchus spp. (for example *D dipsaci*).

The compounds of the invention can be combined with one or more other active pesticide constituents (for example the pyrethroids, carbamates and organophosphates) and/or with attractants, repellents, bactericides, fungicides, nematocides, vermifuges and so on. In addition, it has been observed that the activity of the compounds of the invention can be increased by the addition of a synergist or potentialization agent, for example a synergist of the class of oxydase inhibitors, such as piperonylbutoxide or propyl 2-propynylphenyl phosphonate, by the addition of a second compound of the invention or a pesticide pyrethroid. When an oxydase inhibitor synergist is present in a composition of the invention, the ratio of the synergist to the compound of formula (I) is situated in the range 25:1 to 1:25, for example at approximately 10:1.

The stabilizing agents to prevent any chemical degradation which the compounds of the invention may undergo are in particular, for example, anti-oxidants (such as tocopherols, butylhydroxyanisole, butylhydroxytoluene), vitamin C (ascorbic acid) and oxygen collectors (such as epichlorhydrin), as well as organic and inorganic bases, for example of the trialkylamines such as triethylamine, which can act as basic stabilising agents and collectors.

The compounds of the present invention have pesticide properties and/or an increased photostability and/or a reduced toxicity for mammals.

The following examples illustrate the preferred aspects of the invention in a non-limitative manner.

Preparation 1: 4-(1-fluoro 2-phenyl cyclopropyl) benzoic acid, racemic cis isomer (A)+racemic cis+trans mixture (50/50) (B)

Stage A: tert-butylate 4-formyl benzoate a) 4-formyl benzoic acid chloride 15 g of commercial 4-formyl benzoic acid and 200 $cm^3$ of dichloromethane are mixed together at 0° C. under an inert gas atmosphere, then 9 $cm^3$ of commercial oxalyl chloride and 0.2 $cm^3$ of dimethylformamide are added, the reaction medium is left for half an hour at 0° C. then for 20 hours at ambient temperature, the acid chloride obtained is brought to dryness.

b) tert-butylate 4-formyl benzoate 20 cm$^3$ of tert-butanol and 100 cm$^3$ of pyridine are mixed together at 6° C. under an inert gas atmosphere, then a solution of the residue obtained in Stage a) in 200 cm$^3$ of dimethylformamide is introduced, after one hour at ambient temperature, the reaction medium is heated under reflux for 4 hours then left to return to ambient temperature, the solvent is driven off, the residue is taken up in ethyl acetate, followed by washing and chromatographing on silica. In this way the tert-butyl ester is obtained with a yield of 48.5%.

TLC: $R_f$=0.3 (eluant: heptane-ethyl acetate (8-2)).

Stage B: tert-butyl 4-(hydroxymethyl) benzoate 5.23 g of tert-butyl 4-formyl benzoate obtained according to Stage A is mixed with 100 cm$^3$ of tetrahydrofuran and the mixture is cooled down to 0° C.; 1 g of sodium borohydride is then added, the temperature is left to rise to 20–25° C., agitation is carried out for 3 hours, followed by hydrolysis with 100 cm$^3$ of a 10% aqueous solution of ammonium chloride, extraction with ethyl acetate, the extracts are washed, dried, brought to dryness and the residue is chromatographed on silica (eluant: heptane-ethyl acetate (1-1)).

In this way 5 g of the expected hydroxymethylated derivative is isolated. TLC: $R_f$=0.3 (eluant: heptane-ethyl acetate (1-1)).

Microanalysis $C_{12}H_{16}O_3$=208.3

|  | C % | H % |
|---|---|---|
| Calculated | 69.2 | 7.7 |
| Found | 68.9 | 7.8 |

NMR of the proton in CDCl$_3$ at 250 MHz (in ppm) 1.59 (s): CO$_2$tBu; 2.01 (t): Φ—CH$_2$—OH; 4.75 (d): Φ—CH$_2$—OH 7.40 and 7.96 (AA'BB'): aromatic H's.

IR in CHCl$_3$ in cm$^{-1}$ 3610: OH; 1708: C=O ester; 1613-1576-1505: aromatics.

Stage C: tert-butyl 4-(fluoromethyl) benzoate 4.5 g of tert-butyl 4-(hydroxymethyl) benzoate obtained according to Stage B is mixed with 100 cm$^3$ of dichloromethane under an inert gas atmosphere and the mixture is cooled down to 0° C. 3.56 g of commercial diethylaminosulphur trifluoride (C$_2$H$_5$)$_2$NSF$_3$ known by the abbreviation DAST is then added, the reaction medium is agitated for one hour at 0°/+5° C., then for one hour at 20–25° C., poured into a 10% aqueous solution of sodium bicarbonate, extraction is carried out with dichloromethane, the extracts are dried, brought to dryness and the residue is chromatographed on silica (eluant: methylene chloride). 3 g of the expected fluoromethylated derivative is isolated.

TLC: $R_f$=0.37 (eluant: heptane-ethyl acetate (8-2)).

Microanalysis for $C_{12}H_{15}FO_2$=210.25

|  | C % | H % | F % |
|---|---|---|---|
| Calculated | 68.6 | 7.2 | 9.0 |
| Found | 68.3 | 7.3 | 9.1 |

NMR of the proton in CDCl$_3$ at 250 MHz (in ppm) 1.60 (s): CO$_2$tBu; 5.43 (d, J=47): CH$_2$—F; 7.40 and 8.01 (AA'BB'): aromatic H's.

IR in CHCl$_3$ in cm$^{-1}$ 1712: C=O ester; 1618-1582-1512: aromatics.

Stage D: tert-butyl 4-(bromofluoro methyl) benzoate 2.3 g of tert-butyl 4-(fluoromethyl) benzoate obtained according to Stage C is mixed with 30 cm$^3$ of tetrachloro-methane. 0.1 g of commercial 2,2-azobisisobutyronitrile known by the abbreviation AIBN and 2 g of N-bromo succinimide are added to the mixture, then the whole is taken to reflux and irradiated for 4 hours, a further 0.2 g of AIBN is added, irradiation is carried out for another 4 hours, then the reaction medium is left at rest for 48 hours at ambient temperature. After filtration and chromatography on silica, 1.7 g of the expected bromofluorinated derivative is obtained.

Melting point: 39.4° C.

TLC: $R_f$=0.32 (eluant: heptane-dichloromethane-tert-butyl methyl ether (90-5-5)).

Microanalysis for $C_{12}H_{14}BrFO_2$=289.15

|  | C % | H % | Br % | F % |
|---|---|---|---|---|
| Calculated | 49.85 | 4.9 | 27.6 | 6.6 |
| Found | 50.0 | 4.9 | 27.4 | 6.9 |

NMR of the proton in CDCl$_3$ at 250 MHz (in ppm) 1.6 (s); CO$_2$tBu; 7.43 (d, J=49.5): CHBrF; 7.53–8.04 (AA'BB'): aromatic H's.

IR in CHCl$_3$ in cm$^{-1}$ 1711: C=O ester; 1613-1580-1506: aromatics.

Stage E: (±) tert-butyl 4-(1-fluoro 2-phenyl cyclopropyl) benzoate (cis isomer)

30 cm$^3$ of tetrahydrofuran, 2.2 g of potassium tert-butylate and 4 cm$^3$ of commercial styrene are mixed together under an inert gas atmosphere, then a solution of 3 g of tert-butyl 4-(bromo fluoromethyl) benzoate, obtained according to Stage D, in 30 cm$^3$ of tetrahydrofuran, is added over half an hour; a quarter of an hour later the mixture is poured into a 10% aqueous solution of ammonium chloride, the whole is extracted with ethyl acetate, the extracts are washed, dried, brought to dryness and the residue is chromatographed. Thus 0.25 g of the expected product is obtained.

Melting point: 57.4° C.

TLC: $R_f$=0.15 (eluant: heptane-toluene (50-50))

Microanalysis for $C_{20}H_{21}FO_2$=312.4

|  | C % | H % | F. % |
|---|---|---|---|
| Calculated | 76.9 | 6.8 | 6.1 |
| Found | 76.8 | 6.7 | 5.9 |

NMR of the proton in CDCl$_3$ at 250 MHz (in ppm) 1.6 (s): CO$_2$tBu; 1.5 and 2.0 (m) CH$_2$ in position 3 of the cyclopropane; 2.51 (m): CH in position 2 of the cyclopropane (in trans/F position); 7.31 (m), 8.0 (wd): H of the phenylene; 7.31 (m): H of the phenyl.

IR in CHCl$_3$ in cm$^{-1}$ 1370; 1707: CO$_2$tBu; 1614, 1606, 1575, 1511, 1500: Φ.

MS: M$^+$=312$^+$

By operating in an analogous manner, the following isomer compound mixture was also obtained:

-tert-butyl 4-(1-fluoro 2-phenyl cyclopropyl) benzoate (cis+trans isomers; cis/trans=70/30), racemic.

Stage F: 4-(1-fluoro 2-phenyl cyclopropyl) benzoic acid (cis+trans isomers; cis/trans=70/30), racemic 1 g of tert-butyl 4-(1-fluoro 2-phenyl cyclopropyl) benzoate cis/trans=70/30 racemic obtained according to Stage E is mixed with 80 cm$^3$ of toluene; 0.09 mg para-toluenesulphonic acid monohydrate is added to the mixture, the whole is heated for 6 hours at 100° C. then left at rest overnight. After washing, extraction with ethyl acetate, drying and evaporation to dryness, 1 g of a white solid is obtained (cis/trans isomer=70/30, racemic).

Stage G: 4-(1-fluoro 2-phenyl cyclopropyl) benzoic acid, racemic cis isomer (A)+mixture racemic cis+racemic trans (50/50) (B)

The gram of white solid obtained above is recrystallized from isopropyl ether. 0.39 g of the racemic pure cis isomer (A) is obtained which precipitates and 0.5 g of the cis/trans mixture (50/50) (B) is obtained after having brought the mother liquors to dryness.

Analysis of isomer (A)
Melting point: 169.2° C.
Microanalysis for $C_{16}H_{13}FO_2=256.3$

|  | C % | H % | F % |
|---|---|---|---|
| Calculated | 75.0 | 5.1 | 7.4 |
| Found | 74.7 | 5.0 | 7.3 |

NMR of the proton in CDCl$_3$ at 250 MHz (in ppm) 1.83 (m) and 2.04 (m): CH$_2$ in position 3 of the cyclopropane; 2.57 (m): CH in position 2 of the cyclopropane; 7.39 and 8.14 (AA',BB'): H of the phenylene group; 7.35 to 7.4 (m): H of the phenyl group.

IR in CHCl$_3$ in cm$^{-1}$ 1725 and 1694: C=O; 1615, 1575, 1512 and 1500: Φ.

MS: M$^+$=312$^+$

EXAMPLE 1

4-(1-fluoro 2-phenyl cyclopropyl) N-isobutyl benzenamide (cis+trans isomers, cis/trans=3/2)

Stage A: preparation of the 4-(1-fluoro 2-phenyl cyclopropyl) benzoic acid chloride 0.35 g of 4-(1-fluoro 2-phenyl cyclopropyl) benzoic acid (mixture (B)), obtained according to Preparation 1, and 20 cm$^3$ of dichloromethane are mixed together under an inert gas atmosphere, the mixture is cooled down to 0° C., 0.207 g of commercial oxalyl chloride and 0.01 cm$^3$ of dimethylformamide are added, the whole is agitated for 3 hours at 20–25° C. and brought to dryness in order to collect the acid chloride.

Stage B: Amidification 10 cm$^3$ of pyridine and 0.2 cm$^3$ of commercial isobutylamine are mixed together under an inert gas atmosphere, the mixture is cooled down to 0° C. then a solution of acid chloride obtained in Stage A in 4 cm$^3$ of dimethylformamide is added; the reaction medium is agitated for 20 hours at 20–25° C., brought to dryness, purified and recrystallized from isopropyl ether in order to isolate 0.3 g of the expected amide.

Melting point: 100° C.
TLC: R$_f$=0.2–0.25 (eluant: heptane-dichloromethane-tert-butyl methyl ether (5-4-1)).
Microanalysis for $C_{20}H_{22}FNO=311.14$

|  | C % | H % | F % | N % |
|---|---|---|---|---|
| Calculated | 77.1 | 7.1 | 6.1 | 4.5 |
| Found | 77.0 | 7.1 | 6.2 | 4.5 |

NMR of the proton in CDCl$_3$ (in ppm) mixture of cis (A) and trans (B) isomers (A)
0.95 and 0.99 (d): CH$_3$ of the isobutyl; 1.68 to 2.10: CH of the isobutyl and CH$_2$ in position 3 of the cyclopropyl; 2.51 (m): CH in position 2 of the cyclopropyl; 3.23: CH$_2$ of the isobutyl; 6.07: NH; 6.95 to 7.36: H of the phenyl group; 7.58 (d) and 7.79 (d): H of the phenylene group.

(B)
3.04 (d,d,d, J=8.5–11.5 and 20): CH in position 2 of the cyclopropyl; 3.30: CH$_2$ of the isobutyl; 6.18: NH.

IR in CHCl$_3$ in cm$^{-1}$ 3465: =C—NH; 1656: C=O; 1616, 1572, 1530 and 1502: Φ.

MS: M$^+$=311$^+$

EXAMPLE 2

4-(1-fluoro 2-phenyl cyclopropyl) N-(2-methyl phenyl) benzenamide (cis+trans isomers, cis/trans=3/1)

Stage A: Preparation of the intermediate acid chloride 0.15 g of the isomer mixture (B) and 0.20 g of the cis isomer (A) of 4-(1-fluoro 2-phenyl cyclopropyl) benzoic acid, obtained according to Preparation 1, and 20 cm$^3$ of dichloromethane, are mixed together under an inert gas atmosphere, the mixture is cooled down to 0° C., then 0.15 cm$^3$ of oxalyl chloride and 0.01 cm$^3$ of dimethylformamide are added to the mixture, agitation is carried out for 3 hours at ambient temperature and the reaction medium is brought to dryness under vacuum in order to collect the acid chloride.

Stage B: Amidification 10 cm$^3$ of pyridine and 0.15 cm$^3$ of commercial ortho-toluidine are mixed together under an inert gas atmosphere and the mixture is cooled down to 0° C. and a solution of the acid chloride obtained in Stage A in 6 cm$^3$ of dimethylformamide is added; the reaction medium is agitated for 24 hours at ambient temperature, brought to dryness and chromatographed on silica in order to obtain 0.43 g of the expected amide.

Melting point: 138.2° C.
TLC: R$_f$=0.3–0.35 (eluant: heptane-dichloromethane-tert-butyl methyl ether (5-4-1)).
Microanalysis for $C_{23}H_{20}FNO=345.4$

|  | C % | H % | F % | N % |
|---|---|---|---|---|
| Calculated | 80.0 | 5.8 | 5.5 | 4.1 |
| Found | 79.9 | 5.9 | 5.4 | 4.0 |

NMR of the proton in CDCl$_3$ at 250 MHz (in ppm) mixture of cis (A) 75% and trans (B) 25% isomers For both isomers 1.70 to 1.87 and 1.93 to 2.10: CH$_2$ in position 3 of the cyclopropane, 6.95 to 8.00: aromatic H's and NH.

For (A):
2.35 (s): CH$_3$ of the Φ—CH$_3$; 2.55 (m): CH in position 2 of the cyclopropane, for (B):
2.30 (s): CH$_3$ of the Φ-CH$_3$; 3.08 (d,d,d; J=8, 5, 11 and 20): CH in position 2 of the cyclopropane, IR in CHCl$_3$ in cm$^{-1}$ 3440: =C—NH; 1677: >C=O; 1614, 1605, 1589, 1571, 1526, 1510 and 1500: Φ.

MS: MH$^+$=346$^+$

Preparation 3: 4-[2-(4-chloro phenyl) cyclopropyl] benzoic acid (trans isomer)

Stage A: 3-(4-bromo phenyl) 1-(4-chloro phenyl) propenone

A mixture prepared from 15.46 g of commercial 4-chloroacetophenone, 18.5 g of 4-bromo benzaldehyde and 75 cm$^3$ of 100% ethanol is heated to 35° C., then after a quarter of an hour a solution of 7.41 g of sodium hydroxide in 37 cm$^3$ of water is added, and the whole is agitated overnight. After filtering and rinsing, 33 g of the expected product is obtained.

TLC: $R_f$=0.65 (eluant: hexane-ethyl acetate (1-1))

Stage B: 5-(4-bromo phenyl) 3-(4-chloro phenyl) 4,5-dihydro pyrazole 25 g of 3-(4-bromo phenyl) 1-(4-chloro phenyl) propenone, obtained according to Stage A, 50 cm³ of hydrazine hydrate and 8 cm³ of water are mixed together, the mixture is taken to reflux for one and a half hours then cooled down to ambient temperature, 200 cm³ of water is added and the precipitate obtained is washed.

Stage C: 1-(4-bromo phenyl) 2-(4-chloro phenyl) cyclopropane (trans isomer)

50 cm³ of diethylene glycol and 2.72 g of potassium hydroxide are added to the crude product obtained according to Stage B, the reaction medium is heated at 240° C. for one and a half hours, then cooled down and poured into water, extraction is carried out with diethyl ether, the extracts are dried and brought to dryness and the residue is chromatographed, in order to obtain, after recrystallization, 7.5 g of the expected product.

Stage D: 4-[2-(4-chloro phenyl) cyclopropyl] benzonitrile 2.0 g of the brominated derivative obtained according to Stage C, 15 cm³ of commercial N-methyl pyrrolidine and 1.17 g of cuprous chloride are mixed together, the mixture is taken to reflux for 24 hours, cooled down to 20° C., extraction is carried out with ethyl ether, the extracts are dried, brought to dryness and the residue is chromatographed on silica. 0.8 g of the expected product is collected.

TLC: $R_f$=0.53 (eluant: ethyl ether-hexane (1-1))

MS: $M^+$=254$^+$

Stage E: 4-[2-(4-chloro phenyl) cyclopropyl] benzoic acid (trans isomer)

0.4 g of the cyanated derivative obtained according to Stage D, 7.5 cm³ of ethanol and 7.5 cm³ of a 10M aqueous solution of sodium hydroxide are mixed together, the mixture is taken to reflux for 12 hours, poured into water, washed, acidified with hydrochloric acid, extracted with ethyl ether, the extracts are dried, brought to dryness and 0.3 g of the expected acid is obtained.

TLC: $R_f$=0.37 (eluant: ethyl ether)

EXAMPLE 3

4-[2-(4-chloro phenyl) cyclopropyl] N-isobutyl benzenamide (trans isomer)

0.3 g of the product obtained according to Preparation 3 is mixed with 5 cm³ of dichloromethane, then 0.1 cm³ of oxalyl chloride and a drop of dimethylformamide are added, agitation is carried out for 2 hours, followed by bringing to dryness, 5 cm³ of dichloromethane is added, the reaction medium is cooled down to −10° C. and 0.1 cm³ of pyridine, 0.1 cm³ of isobutylamine, 5 mg of dimethylaminopyridine and 2 cm³ of dichloromethane are added, and the whole is agitated for one hour at ambient temperature. The reaction medium is then poured into water, followed by washing, drying, filtering then bringing to dryness and purifying.

0.23 g of the expected product is obtained.

Melting point: 136–138° C.

TLC: $R_f$=0.46 (eluant: ethyl ether).

NMR of the proton in CDCl$_3$ at 250 MHz 0.96 (d): CH$_3$ of the isobutyl; 1.52 (m) and 2.16 (m): CH in position 1 and 2 and CH$_2$ in position 3 of the cyclopropyl; 1.80–2.08 (m): CH of the isobutyl; 3.24 (t): CH$_2$ of the isobutyl; 6.15: NH; 7.06 (d), 7.18 (d), 7.25 (d), 7.71 (d): aromatic H's.

MS: $M^+$=328$^+$

Preparation 4: 4-[2-(4-chloro phenyl) 1-fluoro cyclopropyl] benzoic acid (cis isomer)

Stage A: tert-butyl 4-[2-(4-chloro phenyl) 1-fluoro cyclopropyl] benzoate (cis+trans isomers; cis/trans=37/63), racemic, By operating as in Stage E of Preparation 1, using commercial 4-chloro styrene, the desired product is obtained.

Melting point: 110° C. cis product

TLC: cis product 0.5–0.27 (eluant: hexane-toluene (50-50)) trans product 0.27–0.30 (eluant: hexane-toluene (50-50))

NMR of the proton at 250 MHz (in ppm) cis product 2.4–2.45: CH in position 2 of the cyclopropane trans product 3.0–3.05: CH in position 2 of the cyclopropane Stage B: 4-[2-(4-chloro phenyl) 1-fluoro cyclopropyl] benzoic acid (cis isomer)

By operating in an analogous manner starting with the cis isomer of tert-butyl 4-[2-(4-chloro phenyl) 1-fluoro cyclopropyl] benzoate, the desired product is obtained with a yield of 80%.

Melting point: 204° C.

EXAMPLE 4

4-[2-(4-chloro phenyl) 1-fluoro cyclopropyl] N-ethyl N-(2-methyl phenyl) benzenamide (cis isomer)

By operating as in Example 1, starting with the acid prepared according to Preparation 4 and commercial N-ethyl ortho-toluidine, the desired product is obtained.

Melting point: 133° C.

NMR of the proton in CDCl$_3$ at 250 MHz (in ppm) 1.20–1.23–1.26: N—CH$_2$—CH$_3$; 1.68 to 1.86: CH$_2$ in position 3 of the cyclopropyl; 2.18 (s): CH$_3$ of the Φ—CH$_3$; 2.30–2.32–2.34: CH in position 2 of the cyclopropyl; 3.62 to 3.69 and 4.10 to 4.20: N—CH$_2$—CH$_3$; 7.01 to 7.51: aromatic 12H's.

MS: MH$^+$=408$^+$

EXAMPLE 5

4-[2-(4-chloro phenyl) 1-fluoro cyclopropyl] N-isobutyl benzenamide (cis isomer)

By operating as in Example 1, starting with the acid prepared according to Preparation 4 and commercial N-isobutyl amine, the desired product is obtained.

Melting point: 140° C.

NMR of the proton in CDCl$_3$ at 250 MHz (in ppm) 0.99 (d): CH$_3$ of the isobutyl; 1.70 to 1.98 (m): CH$_2$ in position 3 of the cyclopropyl and CH of the isobutyl; 2.47 (m): CH in position 2 of the cyclopropyl (trans/F); 3.30 (m): CH$_2$ of the isobutyl; 6.20 (wt): NH; 7.20 to 7.35: aromatic 6H's; 7.80 (wd): aromatic 2H's.

EXAMPLE 6

4-[2-(4-chloro phenyl) 1-fluoro cyclopropyl] N-(2-methyl phenyl) benzenamide (cis isomer)

By operating as in Example 1, starting with the acid prepared according to Preparation 4 and commercial ortho-toluidine, the desired product is obtained.

Melting point: 172° C.

TLC: $R_f$=0.14 (eluant: hexane-ethyl acetate (8-2)).

Microanalysis for $C_{23}H_{19}ClFNO$=379.866

|  | C % | H % | F % | Cl % | N % |
| --- | --- | --- | --- | --- | --- |
| Calculated | 72.73 | 5.04 | 5.0 | 9.3 | 3.69 |
| Found | 72.5 | 4.9 | 4.8 | 9.5 | 3.6 |

NMR of the proton in CDCl$_3$ at 250 MHz (in ppm) 1.803 to 2.025 (2H): CH$_2$ in position 3 of the cyclopropyl; 2.35 (s) and 2.45 0 2.57 (m) (4H): Φ—CH$_3$ and CH in position 2 of the cyclopropyl (trans/F); 7.13 to 7.98 (13H): aromatic H's and NH IR in $CHCl_3$ in $cm^{-1}$ 3444: =C—NH; 1677: O=C<; 1615, 1589, 1570, 1526, 1510 and 1496: Φ+secondary amide.

Preparation 7: 4-[2-(3,4-dibromo phenyl) 1-fluoro cyclopropyl] benzoic acid (cis isomer)

Stage A: tert-butyl 4-[2-(3,4-dibromo phenyl) 1-fluoro cyclopropyl] benzoate (cis isomers)

By operating as in Stage E of Preparation 1, using commercial 3,4-bromo styrene, the desired product is obtained.

NMR of the proton 1.60 (s): $CO_2tBu$ 7.28 to 8.03: aromatic 7H's

Stage B: 4-[2-(3,4-dibromo phenyl) 1-fluoro cyclopropyl] benzoic acid (cis isomer)

By operating in the same manner as in Stage F of Preparation 1, the desired acid is obtained.

EXAMPLE 7

4-[2-(3,4-dibromo phenyl) 1-fluoro cyclopropyl] N-(2-methyl phenyl) benzenamide (cis isomer) and its optically-active isomers.

By operating as in Example 1, starting with the acid prepared according to Preparation 7 and commercial ortho-toluidine, the desired product is obtained.

Melting point: 158° C.

NMR of the proton in $CDCl_3$ at 250 MHz (in ppm) 1.77 to 2.10: $CH_2$ in position 3 of the cyclopropyl; 2.35 (s): $CH_3$ of the Φ—$CH_3$; 2.46 (d,d,d): CH in position 2 of the cyclopropyl (trans/F); 7.63 (s): NH; 7.12 to 7.92: aromatic 11H's.

Separation of optically-active isomers.

2 g of the product obtained in Example 7 is injected in batches of 500 mg over 260 g of CHIRALPAK AD® phase, 20μ with the heptane-ethanol-methanol 50-30-20 eluant mixture and at a flow rate of 100 ml/min. After distillation of the good fractions, dextrogyrated enantiomer A 830 mg (purity 99%) and levogyrated enantiomer B 850 mg (purity 96.6%) are collected. Enantiomer B is reinjected in batches of 425 mg under the same conditions in order to obtain 780 mg (purity 99.4%)

Controls:

The purities are determined by analytical HPLC on a chiralpak AD® column 25 cm×0.46 cm at a flow rate of 1 ml/min with the same eluant mixture. The detection takes place at 254 nm and the capacity factors are 1.44 and 2.35 respectively for the dextrogyrated and levogyrated enantiomers.

Enantiomer A: alphaD (0.6% in $CHCl_3$)=+261°.
Enantiomer B: alphaD (0.6% in $CHCl_3$)=−257°.

EXAMPLE 8

4-[2-(3,4-dibromo phenyl) 1-fluoro cyclopropyl] N-isobutyl benzenamide (cis isomer)

By operating as in Example 1, starting with the acid prepared according to Preparation 7 and commercial N-isobutyl amine, the desired product is obtained.

Melting point: 132° C.

NMR of the proton in $CDCl_3$ at 250 MHz (in ppm) 0.97 (d), 1.00 (d): $CH_3$ of the isobutyl; 1.63 to 1.98 (3H): $CH_2$ in position 3 of the cyclopropyl and CH of the isobutyl; 2.45 (1H): CH in position 2 of the cyclopropyl (trans/F); 3.25 (t) (2H): $CH_2$ of the isobutyl; 6.05 (f): NH; 7.06 to 7.82 (7H): aromatic H's.

Starting with the trans isomers of the acids prepared according to Preparations 1 to 7, the following compounds are obtained:

EXAMPLE 9

4-[2-(4-chloro phenyl) 1-fluoro cyclopropyl] N-isobutyl benzenamide (trans isomer)

Melting point: 157° C.

NMR of the proton in $CDCl_3$ at 250 MHz (in ppm) 0.96 (d): $CH_3$ of the isobutyl; 1.65 to 2.08 (m): $CH_2$ in position 3 of the cyclopropyl and CH of the isobutyl; 2.99 (d,d,d J=8.5, 11.5 and 20): CH in position 2 of the cyclopropyl (cis/F); 3.24 (t): $CH_2$ of the isobutyl; 6.13 (wt): NH; 6.88 (d) and 7.11 (d): H of the 4-chloro phenyl; 7.16 (d). and 7.61 (d): H of the para-phenylene.

EXAMPLE 10

4-[2-(4-chloro phenyl) 1-fluoro cyclopropyl] N-(2-methyl phenyl) benzenamide (trans isomer)

TLC: $R_f$=0.16 (eluant: hexane-ethyl acetate (8-2)).

IR in $CHCl_3$ in $cm^{-1}$ 3450: C—NH; 1676: O=C; 1615, 1589, 1572, 1526, 1510 and 1495: Φ+secondary amide.

By implementing one of the methods set out on the preceding pages, the following products were prepared.

In the following tables:

The asterisk in front of the Example number indicates that the pure cis isomer has been isolated and the double asterisk indicates that the trans isomer has been isolated, TfO represents the trifluoromethyl sulphonyloxy radical, $Z_2$ represents the 2-(pyrrolydin-1-yl) phenyl radical, THP signifies tetrahydropyranyloxy.

TABLE A

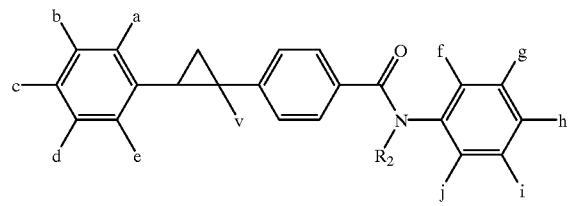

| Ex N°: | a | b | c  | d | e | v | f  | g | h | i | j | $R_2$ |
|--------|---|---|----|---|---|---|----|---|---|---|---|-------|
| 2      | H | H | H  | H | H | F | Me | H | H | H | H | H     |
| 4*     | H | H | Cl | H | H | F | Me | H | H | H | H | Et    |
| 6*     | H | H | Cl | H | H | F | Me | H | H | H | H | H     |
| 7*     | H | Br| Br | H | H | F | Me | H | H | H | H | H     |
| 7A     | H | Br| Br | H | H | F | Me | H | H | H | H | H     |
| 7B     | H | Br| Br | H | H | F | Me | H | H | H | H | H     |

TABLE A-continued

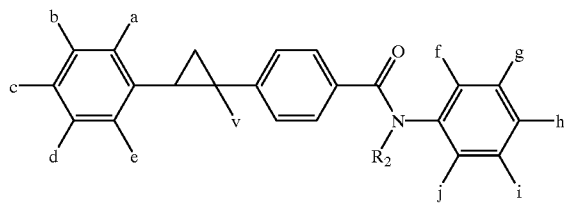

| Ex N°: | a | b | c | d | e | v | f | g | h | i | j | R2 |
|---|---|---|---|---|---|---|---|---|---|---|---|---|
| 10** | H | H | Cl | H | H | F | Me | H | H | H | H | H |
| 12* | H | Cl | Cl | H | H | F | Me | H | H | H | H | H |
| 13* | H | Cl | Cl | H | H | F | Me | H | H | H | H | Et |
| 14** | H | Cl | Cl | H | H | H | Me | H | H | H | H | H |
| 15* | H | Br | Br | H | H | F | Me | H | H | H | H | Et |
| 16* | H | H | MeO | H | H | F | Me | H | H | H | H | Et |
| 17* | H | Cl | Cl | Cl | H | F | Me | H | H | H | H | H |
| 18* | H | CF3 | Br | H | H | F | Me | H | H | H | H | H |
| 19* | Cl | H | Cl | H | H | F | Me | H | H | H | H | H |
| 20 | Cl | H | Cl | H | H | F | Me | H | H | H | H | H |
| 21** | Cl | H | Cl | H | H | F | Me | H | H | H | H | H |
| 22* | H | H | Br | H | H | F | Me | H | H | H | H | H |
| 23* | H | Br | H | H | H | F | Me | H | H | H | H | H |
| 24* | Cl | H | H | H | H | F | Me | H | H | H | H | H |
| 25** | Cl | H | H | H | H | F | Me | H | H | H | H | H |
| 26* | H | PhO | H | H | H | F | Me | H | H | H | H | H |
| 27* | H | PhO | H | H | H | F | Me | H | H | H | H | Et |
| 29* | H | H | Me | H | H | F | Me | H | H | H | H | H |
| 31* | Cl | H | H | H | H | F | Me | H | H | H | H | Et |
| 32* | H | CF3 | Br | H | H | F | Me | H | H | H | H | Et |
| 33* | H | H | CF3 | H | H | F | Me | H | H | H | H | H |
| 34 | H | H | CF3 | H | H | F | Me | H | H | H | H | H |
| 35* | Cl | Cl | H | H | H | F | Me | H | H | H | H | H |
| 36* | Cl | Cl | H | H | H | F | Me | H | H | H | H | Et |
| 37** | H | Br | Br | H | H | F | Me | H | H | H | H | Et |
| 38* | H | H | CF3 | H | H | F | Me | H | H | H | H | Et |
| 39** | H | H | CF3 | H | H | F | Me | H | H | H | H | Et |
| 40* | H | TfO | TfO | H | H | F | Me | H | H | H | H | H |
| 41** | H | Br | Br | H | H | F | Me | H | H | H | H | H |
| 42** | H | H | F | H | H | F | Me | H | H | H | H | H |
| 43* | H | H | F | H | H | F | Me | H | H | H | H | H |
| 44* | H | Br | Br | H | H | F | Me | H | H | H | H | Pr |
| 45* | H | Br | Br | H | H | F | Me | H | H | H | H | Me |
| 46* | Cl | H | H | H | Cl | F | Me | H | H | H | H | H |
| 47* | H | Br | Br | H | H | F | Me | H | H | H | H | Bn |
| 48* | H | Br | Br | H | H | F | Me | H | H | H | H | Bu |
| 49* | H | H | CF3O | H | H | F | Me | H | H | H | H | H |
| 50* | H | H | CHF2O | H | H | F | Me | H | H | H | H | H |
| 51* | H | PhO | F | H | H | F | Me | H | H | H | H | H |
| 52* | H | H | NO2 | H | H | F | Me | H | H | H | H | H |
| 53* | H | F | F | H | H | F | Me | H | H | H | Me | H |
| 56* | H | Br | Br | H | H | F | H | H | tBu | H | H | H |
| 57* | H | Br | Br | H | H | F | CH2=C(CH3) | H | H | H | H | H |
| 58* | H | Br | Br | H | H | F | MeS | H | H | H | H | H |
| 59* | H | Br | Br | H | H | F | MeO | H | H | H | H | H |
| 60* | H | Br | Br | H | H | F | H | H | cyclohexyl | H | H | H |
| 61* | H | Br | Br | H | H | F | Ph | H | H | H | H | H |
| 62* | H | Br | Br | H | H | F | H | Br | H | H | H | H |
| 63* | H | Br | Br | H | H | F | Cl | H | H | H | H | H |
| 64* | H | Br | Br | H | H | F | H | H | H | H | H | H |
| 65* | H | Br | Br | H | H | F | Et | H | H | H | H | H |
| 66* | H | Br | Br | H | H | F | N≡C | H | H | H | H | H |
| 67* | H | Br | Br | H | H | F | CF3O | H | H | H | H | H |
| 68* | H | Br | Br | H | H | F | PhO | H | H | H | H | H |
| 69* | H | Br | Br | H | H | F | Br | H | H | H | H | H |
| 70* | H | Br | Br | H | H | F | H | Cl | MeO | Cl | H | H |
| 71* | H | Br | Br | H | H | F | MeO | H | Cl | Cl | H | H |
| 72* | H | Br | Br | H | H | F | H | H | F | H | H | H |
| 73* | H | Br | Br | H | H | F | H | F | H | H | H | H |
| 74* | H | Br | Br | H | H | F | H | Cl | Br | Cl | H | H |
| 75* | H | Br | Br | H | H | F | NO2 | H | MeO | H | H | H |
| 76* | H | Br | Br | H | H | F | H | Cl | Cl | H | H | H |
| 77* | H | Br | Br | H | H | F | MeO | H | H | Me | H | H |
| 78* | H | Br | Br | H | H | F | H | MeO | H | MeO | H | H |
| 80* | H | Br | Br | H | H | F | H | MeO | MeO | H | H | H |
| 81* | H | Br | Br | H | H | F | Me | H | H | H | Me | Me |

TABLE A-continued

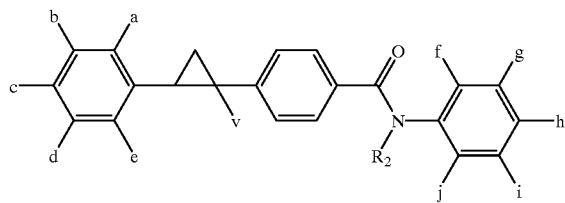

| Ex N°: | a | b | c | d | e | v | f | g | h | i | j | R2 |
|---|---|---|---|---|---|---|---|---|---|---|---|---|
| 82* | H | Br | Br | H | H | F | Me | H | MeO | H | H | H |
| 83* | H | Br | Br | H | H | F | F | H | H | H | F | H |
| 84* | H | Br | Br | H | H | F | H | H | CO2Me | H | H | H |
| 85* | H | Br | Br | H | H | F | H | H | BnO | H | H | H |
| 86* | H | Br | Br | H | H | F | CH3 | H | H | H | Me | H |
| 87* | H | Br | Br | H | H | F | Cl | H | H | H | Cl | H |
| 88* | H | Br | Br | H | H | F | MeO | H | H | CF3 | H | H |
| 89* | H | Br | Br | H | H | F | Me | Me | H | H | H | H |
| 90* | H | Br | Br | H | H | F | Me | H | Me | H | H | H |
| 91* | H | Br | Br | H | H | F | H | MeO | H | CF3 | H | H |
| 92* | H | Br | Br | H | H | F | Cl | H | H | Me | H | H |
| 93* | H | Br | Br | H | H | F | H | H | MeO | H | H | H |
| 94 | H | Br | Br | H | H | F | H | H | PhO | H | H | H |
| 95* | H | Br | Br | H | H | F | F | H | Me | H | H | H |
| 96* | H | Br | Br | H | H | F | H | Cl | Cl | H | H | Me |
| 97* | H | Br | Br | H | H | F | MeO | H | H | MeO | H | H |
| 98* | H | Br | Br | H | H | F | Me | Cl | H | H | H | H |
| 99* | H | Br | Br | H | H | F | H | PhO | H | H | H | H |
| 100* | H | Br | Br | H | H | F | MeO | H | H | NO2 | H | H |
| 101* | H | Br | Br | H | H | F | H | Br | Br | H | H | H |
| 102* | H | Br | Br | H | H | F | PhCO | H | H | H | H | H |
| 103* | H | Br | Br | H | H | F | Cl | H | H | Cl | H | H |
| 104* | H | Br | Br | H | H | F | H | H | NCCH2 | H | H | H |
| 105* | H | Br | Br | H | H | F | Me | H | Me | H | Me | H |
| 106* | H | Br | Br | H | H | F | Cl | H | Cl | H | H | H |
| 107* | H | Br | Br | H | H | F | H | Cl | H | Cl | H | H |
| 108* | H | Br | Br | H | H | F | H | Me | H | Me | H | H |
| 109* | H | Br | Br | H | H | F | Me | H | H | Cl | H | H |
| 110* | H | Br | Br | H | H | F | z2 | H | H | H | H | H |
| 111* | H | Br | Br | H | H | F | CO2Me | H | H | Cl | H | H |
| 112* | H | Br | Br | H | H | F | tBu | H | H | H | H | H |
| 113** | H | Cl | Cl | H | H | H | Me | H | H | H | H | H |
| 114** | H | Cl | Cl | H | H | H | Me | H | H | H | H | Et |
| 115* | H | Cl | Cl | H | H | H | Me | H | H | H | H | H |
| 116 | H | H | Br | H | H | H | Me | H | H | H | H | Et |
| 117** | H | Br | Br | H | H | H | Me | H | H | H | H | H |
| 118 | H | Br | Br | H | H | H | Me | H | H | H | Me | H |
| 119 | H | Cl | Cl | H | H | H | Cl | H | H | H | Cl | H |
| 120* | H | Cl | Cl | H | H | Br | Me | H | H | H | H | H |
| 121* | H | Cl | Cl | H | H | Cl | Me | H | H | H | H | H |
| 268 | H | Br | Br | H | H | F | CHF2O | H | H | H | H | H |
| 269 | H | F | F | H | H | F | Me | H | H | H | H | H |
| 270 | H | Br | TfO | Br | H | F | Me | H | H | H | H | H |
| 271 | H | Br | TfO | H | H | F | Me | H | H | H | H | H |
| 272 | H | Br | TfO | H | H | F | Me | H | H | H | Me | H |
| 274 | H | Br | CHF2O | Br | H | F | Me | H | H | H | Me | H |
| 275 | H | Br | CHF2O | Br | H | F | Me | H | H | H | H | H |
| 276 | H | Br | Br | H | H | F | Cl | H | Me | H | H | H |
| 282 | H | Br | Br | H | H | F | OH | H | H | H | H | H |
| 283 | H | Cl | Cl | H | H | F | CH2OH | H | H | H | H | H |
| 284 | H | Cl | Cl | H | H | F | CH2F | H | H | H | H | H |
| 285 | H | Cl | Cl | H | H | F | CHO | H | H | H | H | H |
| 286 | H | Cl | Cl | H | H | F | Me | H | H | H | Me | H |
| 287 | H | Cl | Cl | H | H | F | Me | H | Me | H | H | H |
| 288 | H | Cl | Cl | H | H | F | F | H | H | H | H | H |
| 289 | H | Cl | Cl | H | H | F | Cl | H | Me | H | H | H |
| 290 | H | Cl | Cl | H | H | F | CN | H | H | H | H | H |
| 291 | H | Cl | Cl | H | H | F | OMe | H | H | CF3 | H | H |
| 292 | H | Br | Br | H | H | F | Me | H | H | H | H | Et |
| 308 | H | Cl | Cl | H | H | F | H | H | PhO | H | H | H |
| 317 | H | Br | Br | H | H | H | Me | H | Me | H | H | H |
| 318 | H | Br | Br | H | H | H | F | H | H | H | H | H |
| 319 | H | Br | Br | H | H | H | Cl | H | Me | H | H | H |
| 320 | H | Br | Br | H | H | H | H | H | PhO | H | H | H |
| 321 | H | Br | Br | H | H | H | H | H | CN | H | H | H |
| 322 | H | Br | Br | H | H | H | OMe | H | H | CF3 | H | H |

TABLE A-continued

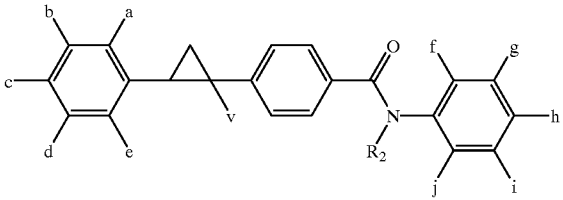

| Ex N°: | a | b | c | d | e | v | f | g | h | i | j | R₂ |
|---|---|---|---|---|---|---|---|---|---|---|---|---|
| 323 | H | Br | Br | H | H | H | CH₂OH | H | H | H | H | H |
| 324 | H | Br | Br | H | H | H | CH₂F | H | H | H | H | H |
| 30* | H | H | MeO | H | H | F | Me | H | H | H | H | H |
| 54* | H | Br | Br | H | F | F | H | H | H | H | H | H |
| 55* | H | Br | Br | H | H | F | H | H | Me | H | H | H |
| 79* | H | Br | Br | H | H | F | MeOC(O) | H | H | H | H | H |
| 273 | H | Br | CHF₂O | H | H | F | Me | H | H | H | H | H |
| 344 | H | H | TfO | H | H | F | Me | H | H | H | H | H |
| 345 | H | Cl | H | Cl | H | F | Me | H | H | H | H | H |
| 346 | H | Br | Br | H | H | F | H | Me | H | H | H | H |

TABLE B

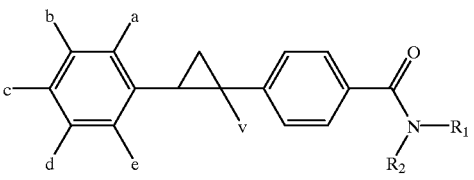

| Ex N°: | a | b | c | d | e | v | R₁ | R₂ |
|---|---|---|---|---|---|---|---|---|
| 1 | H | H | H | H | H | F | (CH₃)₂CHCH₂ | H |
| 3** | H | H | Cl | H | H | H | (CH₃)₂CHCH₂ | H |
| 5* | H | H | Cl | H | H | F | (CH₃)₂CHCH₂ | H |
| 8* | H | Br | Br | H | H | F | (CH₃)₂CHCH₂ | H |
| 9** | H | H | Cl | H | H | F | (CH₃)₂CHCH₂ | H |
| 122** | H | H | F | H | H | F | (CH₃)₂CHCH₂ | H |
| 123* | H | H | F | H | H | F | (CH₃)₂CHCH₂ | H |
| 124* | Cl | H | H | H | Cl | F | (CH₃)₂CHCH₂ | H |
| 125 | Cl | Cl | H | H | H | F | (CH₃)₂CHCH₂ | H |
| 126 | H | F | F | H | H | F | (CH₃)₂CHCH₂ | H |
| 127* | H | H | CHF₂O | H | H | F | (CH₃)₂CHCH₂ | H |
| 128* | H | H | CF₃O | H | H | F | (CH₃)₂CCH₂ | H |
| 129* | H | Br | Br | H | H | F | (CH₃)₂CHCH(CH₃) | CH₃CH₂ |
| 130 | H | Br | Br | H | H | F | CH₃(CH₂)₂ | H |
| 131 | H | Br | Br | H | H | F | (CH₃)₃CH₂C(CH₃)₂ | H |
| 132 | H | Br | Br | H | H | F | CH₃CH₂ | CH₃CH₂ |
| 133 | H | Br | Br | H | H | F | CH₃(CH₂)₃ | H |
| 134 | H | Br | Br | H | H | F | (CH₃)₂CHCH(CH₃) | H |
| 135* | H | Br | Br | H | H | F | (CH₃)₂CHCH₂CH(CH₃) | H |
| 136* | H | Br | Br | H | H | F | (CH₃)₂CHCH₂CH₂ | H |
| 137* | H | Br | Br | H | H | F | CH₃(CH₂)₂ | CH₃ |
| 138* | H | Br | Br | H | H | F | CH₃(CH₂)₅ | H |
| 139* | H | Br | Br | H | H | F | (CH₃)₃CCH(CH₃) | H |
| 140 | H | Br | Br | H | H | F | (CH₃)₃C | H |
| 141* | H | Br | Br | H | H | F | (CH₃)₃CCH₂ | H |
| 142* | H | Br | Br | H | H | F | CH₃CH₂CH(CH₃) | H |
| 143* | H | Br | Br | H | H | F | CH₃CH₂CH(CH₃)CH₂ | H |
| 144* | H | Br | Br | H | H | F | CH₃ | CH₃ |
| 145* | H | Br | Br | H | H | F | (CH₃)₂CH | H |
| 146* | H | Br | Br | H | H | F | CH₃CH₂ | H |
| 147* | H | Br | Br | H | H | F | CH₃CH₂CH(C₂H₅) | H |
| 148* | H | Br | Br | H | H | F | (C₂H₅)CH(CH₃)CH₂CH(CH₃) | H |
| 149* | H | Br | Br | H | H | F | (CH₃)₂CH(CH₂)₃CH(CH₃) | H |
| 150* | H | Br | Br | H | H | F | (CH₃)₃C(CH₂)₂ | H |
| 151* | H | Br | Br | H | H | F | (CH₃)₂CHCH₂ | CH₃ |
| 152* | H | Br | Br | H | H | F | (CH₃)₃C | CH₃ |
| 153* | H | Br | Br | H | H | F | CH₃CH₂C(CH₃)₂ | H |
| 154 | H | Br | Br | H | H | F | CH₃(CH₂)₂CH(CH₃) | H |
| 155 | H | Br | Br | H | H | F | (CH₃)₂CH | (CH₃)₂CH |

TABLE B-continued

| Ex N°: | a | b | c | d | e | v | R₁ | R₂ |
|---|---|---|---|---|---|---|---|---|
| 156 | H | Br | Br | H | H | F | $(CH_3)_2CH$ | Et |
| 157* | H | H | Br | H | H | H | $(CH_3)_2CHCH_2$ | H |
| 158* | H | Br | Br | H | H | H | $(CH_3)_2CHCH_2$ | H |
| 159 | H | Cl | Cl | H | H | H | $(CH_3)_2CHCH(CH_3)$ | H |
| 160** | H | Cl | Cl | H | H | F | $(CH_3)_2CHCH_2$ | H |
| 161* | H | Cl | Cl | H | H | Cl | $(CH_3)_2CHCH_2$ | H |
| 162 | H | Cl | Cl | H | H | Cl | $(CH_3)_2CHCH(CH_3)$ | H |
| 163* | H | Cl | Cl | H | H | Br | $(CH_3)_2CHCH_2$ | H |
| 164* | H | Br | Br | H | H | F | $CH_2{=}C(CH_3)CH_2$ | H |
| 165* | H | Br | Br | H | H | F | $CH_2{=}CHCH_2$ | H |
| 166* | H | Br | Br | H | H | F | $CH{\equiv}CCH_2$ | H |
| 167* | H | Br | Br | H | H | F | $CH_2{=}C(Cl)CH_2$ | H |
| 168* | H | PhO | F | H | H | F | $(CH_3)_2CHCH_2$ | H |
| 169* | H | F | F | H | H | F | $C_6H_5{-}CH(CH_3)$ (R) | H |
| 170* | H | Br | Br | H | H | F | (2-Me $C_6H_4)CH_2$ | H |
| 171* | H | Br | Br | H | H | F | (4-Cl $C_6H_4)CH_2$ | H |
| 172* | H | Br | Br | H | H | F | $(C_6H_5)CH_2$ | H |
| 173 | H | Br | Br | H | H | F | $C_6H_5{-}CH(CH_3)$ | H |
| 174* | H | Br | Br | H | H | F | cyclobutyl | H |
| 175* | H | Br | Br | H | H | F | cyclohexyl | H |
| 176* | H | Br | Br | H | H | F | cyclopentyl | H |
| 177* | H | Br | Br | H | H | F | cyproyl | H |
| 178* | H | Br | Br | H | H | F | (cyclopropyl) methyl | H |
| 179* | H | Br | Br | H | H | F | $C_6H_5{-}CH_2(CH_2)_3$ | H |
| 180 | H | Br | Br | H | H | F | (3-$CF_3$ $C_6H_4)CH_2C(CH_3)$ | H |
| 181* | H | Br | Br | H | H | F | (cyclohexyl) methyl | H |
| 182 | H | Br | Br | H | H | F | adamantyl | H |
| 183* | H | Br | Br | H | H | F | 2-methyl cyclohexyl | H |
| 184* | H | Br | Br | H | H | F | $CH{\equiv}CC(CH_3)_2$ | H |
| 185* | H | Br | Br | H | H | F | 2,3-dihydro 1-indenyl | H |
| 186* | H | Br | Br | H | H | F | 1-naphthyl | H18 |
| 187* | H | Br | Br | H | H | F | $N{\equiv}CCH_2$ | H |
| 188 | H | Br | Br | H | H | F | (2-thienyl) methyhl | H |
| 190* | H | Br | Br | H | H | F | 4(R)-tBu cyclohexyl | HH |
| 192* | H | Br | Br | H | H | F | $tBuOC({=}O)CH_2$ | H |
| 193* | H | Br | Br | H | H | F | $MeSCH_2CH_2$ | H |
| 194* | H | Br | Br | H | H | F | $ClCH_2(CH_2)_2$ | H |
| 195 | H | Br | Br | H | H | F | 2-(1,4-oxazin-1-yl) ethyl | H |
| 196* | H | Br | Br | H | H | F | $CF_3CH_2$ | H |
| 197* | H | Br | Br | H | H | F | $(C_7F_{15})CH_2$ | H |
| 198* | H | Br | Br | H | H | F | (oxolann-2-yl) methyl | H |
| 199* | H | Br | Br | H | H | F | 4-Me thiazol-2-yl | H |
| 200* | H | Br | Br | H | H | F | $(C_6H_5)_2CH$ | H |
| 201* | H | Br | Br | H | H | F | $(C_6H_5)CH_2CH(C_6H_5)$ | H |
| 202* | H | Br | Br | H | H | F | $(C_6H_5)_2CHCH_2$ | H |
| 203* | H | Br | Br | H | H | F | $(MeO)_2CHCH_2$ | H |
| 204* | H | Br | Br | H | H | F | $MeOCH_2CH_2$ | H |
| 205* | H | Br | Br | H | H | F | 3-(2-oxo pyrrolidino) propyl | H |
| 206* | H | Br | Br | H | H | F | $CH_2{=}C(Br)CH_2$ | H |
| 207* | H | Br | Br | H | H | F | $FCH_2CH_2$ | H |
| 208* | H | Br | Br | H | H | F | $[MeOC({=}O)] (C_6H_5)CH$ | H |
| 209* | H | Br | Br | H | H | F | (1-Et pyrrolidin-2yl) methyl | H |
| 210* | H | Br | Br | H | H | F | 5-Me isoxazol-3-yl | H |
| 211* | H | Br | Br | H | H | F | $CH_2(OH)CH(CH_3)$ | H |
| 212 | H | Cl | Cl | H | H | H | cyclobutyl | H |
| 213 | H | Br | Br | H | H | F | (4-Me thiazol-5-yl) methyl | Me |
| 214 | Br | Br | H | H | F | | $(CH_3)_2NCH_2CH_2CH_3$ | |
| 215* | H | Br | Br | H | H | F | $(CH_3)_2NCH_2CH(CH_3)$ | H |
| 216* | H | Br | Br | H | H | F | $(CH_3)_2NCH_2CH_2$ | H |
| 217* | H | Br | Br | H | H | F | $(CH_3)_2CH$ | $(CH_3)_2CH$ |
| 218* | H | Br | Br | H | H | F | $(CH_3)_2CH$ | $CH_3CH_2$ |
| 219* | H | Br | Br | H | H | F | N(R₁) (R₂): 1,4-thiazin-4-yl | |
| 220* | H | Br | Br | H | H | F | N(R₁) (R₂): aziridin-1-yl | |
| 221 | H | Br | Br | H | H | F | N(R₁) (R₂): piperidin-1-yl | |
| 222 | H | Br | Br | H | H | F | N(R₁) (R₂): pyrrolidin-1-yl | |
| 223 | H | Br | Br | H | H | F | N(R₁) (R₂): 1,4-oxazin-4-yl | |
| 224 | H | Br | Br | H | H | F | N(R₁) (R₂): 2-Me piperidin-1-yl | |

TABLE B-continued

| Ex N°: | a | b | c | d | e | v | R₁ | R₂ |
|---|---|---|---|---|---|---|---|---|
| 225 | H | Br | Br | H | H | F | pyrrolidin-1-yl | H |
| 226* | H | Br | Br | H | H | F | 1,4-oxazin-4-yl | H |
| 227 | H | Br | Br | H | H | F | (3,5-diCl C₆H₃)NH | H |
| 228* | H | Br | Br | H | H | F | piperidin-1-yl | H |
| 229* | H | Br | Br | H | H | F | (CH₃)₂N | H |
| 277 | H | Br | Br | H | H | F | (1,5-diMe)piperidinyl-1-yl | H |
| 278 | H | Br | TfO | Br | H | F | CH₃CH(CH₃)CH₂ | H |
| 279 | H | Br | CHF₂O | Br | H | F | CH₃CH(CH₃)CH₂ | H |
| 280 | H | Br | Br | H | H | F | pyridin-3-yl | H |
| 281 | H | Br | Br | H | H | F | N(R₁) (R₂): 2-CH₂OH pyrrolidin-1-yl | |
| 293 | H | Br | Br | H | H | F | 2-Cl 3-pyridinyl | H |
| 294 | H | Cl | Cl | H | H | F | benzazetidine | H |
| 295 | H | Cl | Cl | H | H | F | (CH₃)₃CCH₂C(CH₃)₂ | H |
| 296 | H | Cl | Cl | H | H | F | C₆H₅—CH₂CH₂CH₂CH₂ | H |
| 297 | H | Cl | Cl | H | H | F | N(R₁) (R₂): 1,4-oxazin-4-yl | |
| 298 | H | Cl | Cl | H | H | F | (CH₃)₂CHCH₂ | H |
| 299 | H | Cl | Cl | H | H | F | (CH₃)₂CHCH(CH₃) | H |
| 300 | H | Cl | Cl | H | H | F | cyclopentyl | H |
| 301 | H | Cl | Cl | H | H | F | 1,4-oxazin-4-yl | H |
| 302 | H | Cl | Cl | H | H | F | H | H |
| 303 | H | Cl | Cl | H | H | F | (CH₃)₂C=CHCH₂ | H |
| 304 | H | Cl | Cl | H | H | F | CH₂=C(CH₃)CH₂ | H |
| 305 | H | Cl | Cl | H | H | F | Cl—CH₂CH₂CH₂ | H |
| 306 | H | Cl | Cl | H | H | F | (CH₃)₂CHCH₂CH₂ | H |
| 307 | H | Cl | Cl | H | H | F | CH₃ | H |
| 309 | H | Cl | Cl | H | H | F | CH₂=C(Br)CH₂ | H |
| 310 | H | Cl | Cl | H | H | F | CH₃—S—CH₂CH₂ | H |
| 311 | H | Cl | Cl | H | H | F | C≡CCH₂ | H |
| 312 | H | Cl | Cl | H | H | F | C₆H₅—CH(CH₃) | H |
| 313 | H | Cl | Cl | H | H | F | (CH₃)₂NCH₂CH₂ | CH₃ |
| 314 | H | Cl | Cl | H | H | F | 2-THP | H |
| 315 | H | CL | Cl | H | H | F | cyclohex-3-en-1-yl | H |
| 316 | H | Cl | Cl | H | H | F | tetrazole | H |
| 325 | H | Br | Br | H | H | H | (CH₃)₃CCH₂C(CH₃)₂ | H |
| 326 | H | Br | Br | H | H | H | C₆H₅—CH₂CH₂CH₂CH₂ | H |
| 327 | H | Br | Br | H | H | H | N(R₁) (R₂): 1,4-oxazin-4-yl | |
| 328 | H | Br | Br | H | H | H | (CH₃)₂CHCH₂ | H |
| 329 | H | Br | Br | H | H | H | (CH₃)₂CHCH(CH₃) | H |
| 330 | H | Br | Br | H | H | H | cyclopentyl | H |
| 331 | H | Br | Br | H | H | H | 1,4-oxazin-4-yl | H |
| 332 | H | Br | Br | H | H | H | CH₂=C(CH₃)CH₂ | H |
| 333 | H | Br | Br | H | H | H | (CH₃)₂CHCH₂CH₂ | H |
| 334 | H | Br | Br | H | H | H | CH₃ | H |
| 335 | H | Br | Br | H | H | H | CH₂=C(Br)CH₂ | H |
| 336 | H | Br | Br | H | H | H | CH₃SCH₂CH₂ | H |
| 337 | H | Br | Br | H | H | H | CH≡CCH₂ | H |
| 338 | H | Br | Br | H | H | H | C₆H₅—CH(CH₃) | H |
| 339 | H | Br | Br | H | H | H | (CH₃)₂NCH₂CH₂ | CH₃ |
| 340 | H | H | TfO | H | H | F | cyclobutyle | H |
| 341 | H | H | TfO | H | H | F | (CH₃)₂CHCH(CH₃) | H |

TABLE C

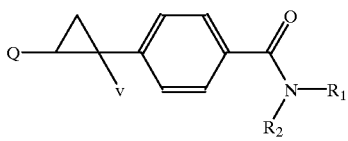

| Ex N: | Q | V | R₁ | R₂ |
|---|---|---|---|---|
| 230** | 5-bromo 2-naphtyl | F | 2-methyl phenyl | ethyl |
| 231* | 5-bromo 2-naphtyl | F | 2-methyl phenyl | ethyl |
| 232* | 5-bromo 2-naphtyl | F | 2-methyl phenyl | H |
| 233** | 5-bromo 2-naphtyl | F | 2-methyl phenyl | H |
| 234* | 2-naphthyl | F | 2-methyl phenyl | H |
| 235* | 2-naphthyl | F | 2-methyl propyl | H |
| 236* | 6-bromo 1-naphthyl | F | 2-methyl phenyl | H |
| 237 | 6-bromo 1-naphthyl | F | 2-methyl propyl | H |
| 238 | 6-bromo 1-naphthyl | F | 1,2-dimethyl propyl | H |
| 239 | 7-bromo 1-naphthyl | F | 2-methyl propyl | H |

TABLE D

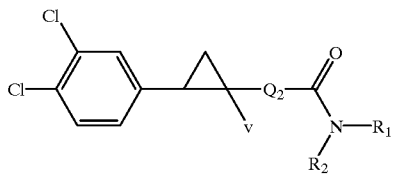

(In the following table the phenylene radicals are bonded to the amide function by the carbon in position 1 and the naphtylene radicals by the carbons in positions 1 or 2)

| Ex N°: | Q₂ | v | R₁ | R₂ |
|---|---|---|---|---|
| 240* | 1,3-phenylene | F | 2-methyl phenyl | H |
| 240** | 1,3-phenylene | F | 2-methyl phenyl | H |
| 241** | 1,3-phenylene | F | 2-methyl phenyl | CH₃CH₂ |
| 242* | 1,3-phenylene | F | 2-methyl phenyl | CH₃CH₂ |
| 243* | 1,3-phenylene | F | 2-methyl propyl | H |
| 244* | 2-methyl 1,4-phneylene | F | 2-methyl phenyl | H |
| 245* | 2-methyl 1,4-phneylene | F | 2-methyl propyl | H |
| 246 | 2-methyl 1,4-phneylene | CH₃ | 2-methyl phenyl | H |
| 247** | 2,3,5,6-tetrafluoro 1,4-phenylene | F | 2-methyl phenyl | H |
| 248* | 3-methyl 1,4-phenylene | F | 2-methyl phenyl | H |
| 249* | 2-methyl 1,4-phenylene | F | 2-methyl propyl | H |
| 250* | 2-chloro 1,4-phenylene | F | 2-methyl phenyl | H |
| 251* | 2,5-naphthylene | F | 2-methyl phenyl | H |
| 252* | 2,5-naphthylene | F | 2-methyl propyl | H |
| 253* | 1,5-naphthylene | F | 2-methyl phenyl | H |
| 254* | 1,5-naphthylene | F | 2-methyl propyl | H |
| 255* | 2-acetylamino 5-chloro 1,4-phenylene | F | 2-methyl phenyl | H |
| 256* | 2-amino 5-chloro 1,4-phenylene | F | 2-methyl phenyl | H |
| 257** | 2,3,5,6-tetrafluoro 1,4-phenylene | H | 2-methyl phenyl | CH₃CH₂ |
| 258** | 2-chloro 1,4-phenylene | H | 2-methyl phenyl | H |
| 259** | 2-chloro 1,4-phenylene | H | 2-methyl propyl | H |
| 260* | 3-fluoro 1,4-phenylene | H | 2-methyl phenyl | H |
| 261* | 3-fluoro 1,4-phenylene | H | 2-methyl propyl | H |
| 342 | 1,4-naphthylene | H | 2-methyl phenyl | H |
| 343 | 5-Cl 2(1-methyl-ethylidene)amino 1,4-phenylene | F | 2-methyl phenyl | H |

TABLE E

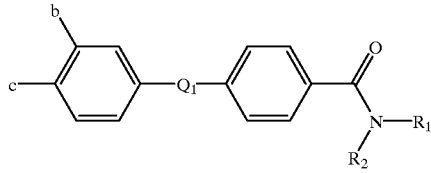

(In the following table, the position 1 of Q₁ is bonded to the anilide group)

| Ex N°: | b | c | Q₁ | R₁ | R₂ |
|---|---|---|---|---|---|
| 262 | Br | Br | 3,3-dibromo 1,2-cyclo-propanediyl | 2-methyl phenyl | H |
| 263 | H | Cl | 1,2-difluoro 1,2-cyclo-propanediyl | 2-methyl phenyl | H |

TABLE F

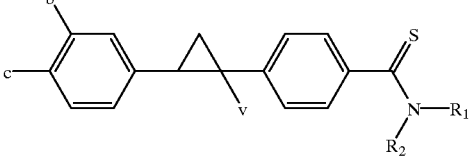

| Ex N°: | b | c | v | R₁ | R₂ |
|---|---|---|---|---|---|
| 264 | Br | Br | F | 2-methyl phenyl | H |
| 265 | Br | Br | F | 1,2-dimethyl propyl | H |
| 345 | Br | Br | F | 2-methyl phenyl | H |

In the table below, the physical analysis results of products of formula (I) are given.

| Products of examples | M.p. ° C. | Rf |
|---|---|---|
| 4 | 133° C. | 0,19 (hexane/AcOEt 7/3) |
| 6 | 172° C. | 0,14 (hexane/AcOEt 8/2) |
| 7 | 158° C. | 0,2 (hexane/AcOEt 7/3) |
| 12 | 148° C. | 0,2 (hexane/AcOEt 7/3) |
| 13 | 126.8° C. | 0,18 (hexane/AcOEt 7/3) |
| 15 | 130.1° C. | 0,07 (ether isopropylique/heptane/1/1) |
| 17 | 195° C. | 0,25 (heptane/AcOEt 7/3) |
| 20 | — | 0,1 (heptane/AcOEt 85/15) |
| 23 | 128° C. | 0,16 (heptane/AcOEt 7/3) |
| 32 | — | 0,12 (heptane/AcOEt 7/3) |
| 33 | — | 0,25 (heptane/AcOEt 7/3) |
| 38 | — | 0,13 (heptane/AcOEt 7/3) |
| 45 | 147° C. | 0,18 (hexane/AcOEt 7/3) |
| 47 | 107.8° C. | 0,18 (hexane/AcOEt 8/2) |
| 49 | 137° C. | — |
| 50 | 124° C. | 0,45 (heptane/AcOEt 7/3) |
| 54 | 138.1° C. | 0,25 (heptane/AcOEt 7/3) |
| 72 | — | 0,22 (heptane/AcOEt 7/3) |
| 73 | — | 0,25 (heptane/AcOEt 7/3) |
| 82 | — | 0,08 (heptane/AcOEt 7/3) |
| 86 | — | 0,24 (hexane/AcOEt 7/3) |
| 105 | — | 0,48 (hexane/AcOEt 7/3) |
| 113 | 156.6° C. | 0,3 (heptane/AcOEt 1/1) |
| 114 | 122.3° C. | 0,25 (heptane/AcOEt 1/1) |
| 117 | 163.6° C. | 0,32 (heptane/AcOEt 1/1) |
| 121 | 141° C. | 0,1 (heptane/AcOEt 8/2) |
| 284 | 164° C. | 0,15 (heptane/Etheriso 1/1) |
| 292 | — | 0,5 (heptane/AcOEt 1/1) |

-continued

| Products of examples | M.p. °C. | Rf |
|---|---|---|
| 8 | 132° C. | 0,17 (hexane/AcOEt 7/3) |
| 128 | 139° C. | 0,14 (hexane/AcOEt 7/3) |
| 167 | 136° C. | 0,15 (hexane/AcOEt 7/3) |
| 174 | 189.9° C. | 0,23 (heptane/AcOEt 1/1) |
| 194 | — | 0,2 ($CH_2Cl_2$) |
| 226 | — | 0,02 (heptane/AcOEt 7/3) |
| 293 | — | 0,25 ($CH_2Cl_2$/TEA 99/1) |
| 231 | — | 0,2 (heptane/AcOEt 7/3) |
| 232 | — | 0,25 (heptane/AcOEt 7/3) |
| 236 | 184° C. | 0,32 (heptane/dioxane 6/4) |
| 244 | 159° C. | 0,24 (heptane/AcOEt 7/3) |
| 264 | — | 0,42 (heptane/AcOEt 1/1) |
| 265 | — | 0,28 (hexane/AcOEt 7/3) |

Preparations of compositions.

In the examples of compositions hereafter, the following signs mean:

* Surfactant.

Reacts by forming the polyurea walls of the microcapsules.

1. Emulsifiable concentrate.

| | |
|---|---|
| Active ingredient | 10.00 |
| Ethoxylated alkylphenol* | 7.50 |
| Alklarylsulphonate* | 2.50 |
| C8–13 aromatic solvent | 80.00 |
| | 100.00 |

2. Emulsifiable concentrate.

| | |
|---|---|
| Active ingredient | 10.00 |
| Ethoxylated alkylphenol* | 2.50 |
| Alkylarylsulphonate* | 2.50 |
| Ketonic solvent | 64.00 |
| C8–13 aromatic solvent | 18.00 |
| Antioxidant | 3.00 |
| | 100.00 |

3. Wettable powder.

| | |
|---|---|
| Active ingredient | 5.00 |
| C8–13 aromatic solvent | 7.00 |
| C18 aromatic solvent | 28.00 |
| Kaolin | 10.00 |
| Alkylarylsulphonate* | 1.00 |
| Naphthalenesulphonic acid* | 3.00 |
| Diatomaceous earth | 46.00 |
| | 100.00 |

4. Dusting powder.

| | |
|---|---|
| Active ingredient | 0.50 |
| Talc | 99.50 |
| | 100.00 |

5. Bait.

| | |
|---|---|
| Active ingredient | 0.5 |
| Sugar | 79.5 |
| Paraffin wax | 20.0 |
| | 100.00 |

6. Concentrate in emulsion.

| | |
|---|---|
| Active ingredient | 5.00 |
| C8–13 aromatic solvent | 32.00 |
| Cetyl alcohol | 3.00 |
| Polyoxyethyleneglycerol monooleate* | 0.75 |
| Polyoxyethylenesorbitan esters* | 0.25 |
| Silicon solution | 0.1 |
| Water | 58.9 |
| | 100.00 |

7. Concentrate in suspension.

| | |
|---|---|
| Active ingredient | 10.00 |
| Ethoxylated alkylphenol* | 3.00 |
| Silicon solution | 0.1 |
| Alkanediol | 5.0 |
| Fumed silica | 0.50 |
| Xanthan gum | 0.20 |
| Water | 80.0 |
| Buffer | 1.2 |
| | 100.00 |

8. Microemulsion.

| | |
|---|---|
| Active ingredient | 10.00 |
| Polyoxyethyleneglycerol monooleate* | 10.00 |
| Alkanediol | 4.00 |
| Water | 76.00 |
| | 100.00 |

9. Granules dispersible in water.

| | |
|---|---|
| Active ingredient | 70.00 |
| Polyvinylpyrrolidine | 2.50 |
| Ethoxylated alkylphenol | 1.25 |
| Alkylarylsulphonate | 1.25 |
| Kaolin | 25.00 |
| | 100.00 |

10. Granules.

| | |
|---|---|
| Active ingredient | 2.00 |
| Ethoxylated alkylphenol* | 5.00 |
| Alkylarylsulphonate* | 3.00 |
| C8–13 aromatic solvent | 20.00 |
| Kieselguhr granules | 70.00 |
| | 100.00 |

11. Aerosol (spray).

| | |
|---|---|
| Active ingredient | 0.3 |
| Piperonylbutoxide | 1.5 |
| C8–13 saturated hydrocarbon solvent | 58.2 |
| Butane | 40.0 |
| | 100.00 |

12. Aerosol (spray).

| | |
|---|---|
| Active ingredient | 0.3 |
| C8–13 saturated hydrocarbon solvent | 10.0 |
| Sorbitan monooleate* | 1.0 |
| Water | 40.0 |
| Butane | 48.7 |
| | 100.00 |

13. Aerosol (spray).

| | |
|---|---|
| Active ingredient | 1.00 |
| $CO_2$ | 3.00 |
| Polyoxyethyleneglycerol monooleate* | 1.40 |
| Propanone | 38.00 |
| Water | 56.60 |
| | 100.00 |

14. Varnishes.

| | |
|---|---|
| Active ingredient | 2.50 |
| Resin | 5.00 |
| Antioxidant | 0.50 |
| Very aromatic white spirit | 92.0 |
| | 100.00 |

15. Spray (ready-to-use).

| | |
|---|---|
| Active ingredient | 0.10 |

|  |  |
|---|---|
| *-continued* | |
| Antioxidant | 0.10 |
| Odourless kerosene | 99.8 |
|  | 100.00 |
| 16. Potentialized spray (ready-to-use). | |
| Active ingredient | 0.10 |
| Piperonylbutoxide | 0.50 |
| Antioxidant | 0.10 |
| Odourless kerosene | 99.30 |
|  | 100.00 |
| 17. Microcapsules. | |
| Active ingredient | 10.0 |
| C8–13 aromatic solvent | 10.0 |
| Aromatic diisocyanate # | 4.5 |
| Ethoxylated alkylphenol* | 6.0 |
| Alkyldiamine # | 1.0 |
| Diethylenetriamine | 1.0 |
| Concentrated hydrochloric acid | 2.2 |
| Xanthan gum | 0.2 |
| Fumed silica | 0.5 |
| Water | 64.6 |
|  | 100.00 |
| 18. Dispersible concentrate. | |
| Active ingredient | 5.0 |
| N-methylpyrrolidinone | 15.00 |
| N-alkylpyrrolidinone | 53.00 |
| C8–13 aromatic solvent | 16.00 |
| Nonylphenol polyoxyethylenic ether phosphate | 6.00 |
| Ethoxylated alkylphenol | 3.50 |
| Alkylarylsulphonate | 1.30 |
| Polyalkyleneglycol ether | 0.20 |
|  | 100.00 |
| 19. Soluble concentrate. A homogeneous mixture is made of: | |
| Active ingredient | 0.25 |
| Piperonyl butoxide | 1.00 |
| Tween 80 | 0.25 |
| Topanol A | 0.1 |
| Water | 98.40 |
| 20. Emulsifiable concentrate. The following are intimately mixed: | |
| Active ingredient | 0.015 |
| Piperonyl butoxide | 0.5 |
| Topanol A | 0.1 |
| Tween 80 | 3.5 |
| Xylene | 95.885 |

*Surfactant.
Reacts by forming the polyurea walls of the micro-capsules.

BIOLOGICAL STUDY

A) Study on Phaedon cochleariae

The product is dissolved at the desired concentration in an acetone-water (50-50) mixture. Foliar discs of Chinese cabbage (*Brassica pekinensis*) are immersed for five seconds in the solution, then left to dry for one hour. Ten adults (a mixture of male and female) are put in a Petri dish each 5containing a foliar disc. The dishes are kept at a temperature of 25° C., with a photoperiod of twelve hours. After seven days, the mortality of the insects is checked, and the surface area of the leaves consumed is evaluated.

The following products have a good activity starting from a dose of 30 ppm: products of Examples 1, 4, 5, 6, 7, 8, 12, 13, 17, 18, 231, 232, 45, 128, 226, 86, 87, 141, 145, 194, 105, 284, 264, 292.

B) Study on *Spodoptera littoralis*

The product is dissolved at the desired concentration in an acetone-water (50-50) mixture. Bean leaves (*Phaseolus vulgaris*, Delinel var.) are immersed for five seconds in the solution, then left to dry in a Petri dish for one hour. Ten *Spodoptera littoralis* larvae are then put in each dish. The dishes are kept at a temperature of 250C, with a photoperiod of twelve hours. After seven days, the mortality of the larvae is checked, and the surface area of the leaves consumed is evaluated.

The following products have a good activity starting from a dose of 30 ppm: products of Examples 4, 5, 6, 7, 8, 12, 13, 15, 17, 18, 20, 22, 23, 32, 33, 38, 44, 45, 47, 48, 49, 50, 128, 129, 344, 236, 345, 54, 174, 175, 178, 63, 346, 15 176, 65, 66, 134, 69, 72, 73, 226, 82, 83, 86, 87, 89, 90, 141, 142, 228, 143, 145, 293, 206, 105, 167, 284, 113, 114, 30117, 159, 212, 264, 292, 121, 265, 345.

C) Study on *Heliothis virescens*

The product is dissolved at the desired concentration in an acetone-water (50-50) mixture. 50 ul of solution is deposited on the surface of a small well containing about 2 grams of vegetable-based artificial medium. A neonate larva of Heliothis virescens is then put into each well, which is sealed with a sheet of cellophane. The tests are kept at a temperature of 25° C., with a photoperiod of twelve hours. The mortality of the larvae is checked after seven days.

The following products have a good activity starting from a dose of 30 ppm: products of Examples 4, 5, 6, 7, 12, 30 22, 32, 33, 38, 49, 50, 54, 175, 63, 65, 69, 72, 83, 86, 89, 90, 105, 284, 117, 244, 292, 345.

D) Study of the activity on Diabrotica

The test insects are final-stage larvae of *Diabrotica undecimpunctata*.

A disc of 9 cm diameter filter paper, placed at the bottom of a Petri dish, is treated using 1 cm³ of acetonic solution. After drying, 15 larvae per dose are deposited and the mortality check is carried out 24 hours after the treatment.

The following products have a good activity starting from a dose of 30 ppm: products of Examples 134, 81, 86.

What is claimed is:

1. A compound in all its stereoisomeric forms or in the form of mixtures of these stereoisomers of the formula

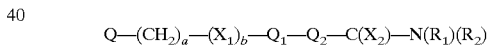

wherein Q is aryl or a group derived from a condensed bicyclic hydrocarbon containing a benzene ring which is linked to an adjacent $(CH_2)_a$ by a carbon atom of said benzene ring, Q contains 6 to 12 carbon atoms unsubstituted or substituted with at least one member of the group consisting of halogen, methylenedioxy, difluoromethylenedioxy, tetrafluoroethylenedioxy, —CN, —NO₂, cyanato, thiocyanato, pentafluorothio, fluorosulfonyl and R—(T)$_c$, R is selected from the group consisting of hydrogen, aliphatic of up to 8 carbon atoms, aryl of up to 8 carbon atoms and cycloaliphatic of up to 8 carbon atoms, c is 0 or 1, T is selected from the group consisting of oxy, carbonyl, carbonyloxy, oxycarbonyl, thio, sulfinyl, sulfonyl, sulfonyloxy, —(CO)$_d$—NR'—, (CO)$_e$—(O)$_f$— and —NR"—S—(O)$_g$—, d, e and f are individually 0 or 1, f is 0 when e is 0, the sum of d+e is 0 or 1, g is 0 or 1 or 2, R' and R" are one of the definitions of R, a and b are individually 0 or 1, $X_1$ is selected from the group consisting of bivalent oxy, thio, sulfinyl and sulfonyl, $X_2$ is oxygen or sulfur, $Q_1$ is cyclopropanediyl optionally unsubstituted or substituted with at least one member of the group consisting of halogen, —CN, azido and aliphatic of up to 4 carbon atoms, Q₂ is arylene radical or a group derived from a condensed bicyclic hydrocarbon containing a benzene ring, which is linked to the adjacent Q₁ and C(X₂) groups by two carbon atoms of said benzene ring, Q₂ contains 6 to 12 carbon atoms and be independent of Q, unsubstituted or substituted, R₁ and R₂ together with the nitrogen atom to which they are attached form a nitrogenous heterocycle of 3 to 10 ring members optionally containing at least one ring heteroatoms chosen from the group consisting of oxygen, nitrogen and sulfur and optionally substituted with at least one member of the group consisting of halogen, methylenedioxy, difluoromethylenedioxy, tetra-fluoroethylenedioxy, —CN, —NO₂, —NH₂, alkylamino and alkenylamino of up to 4 carbon atoms, cyanato, thiocyanato, pentafluorothio, pentafluorosulfonyl and R—(T)$_c$ and R, T, R', R", c, d, e, f and g are defined as above.

2. A compound of claim 1 wherein Q is phenyl or naphthyl optionally having up to 3 substituents.

3. A compound of claim 1 wherein R₁ and R₂ form a member selected from the group consisting of 1,4-thiazin-4-yl, 1,4-oxazin-4-yl, 1-aziridinyl, 1-piperidinyl, 1-pyrrolidinyl, 2-methylpiperidin-1-yl and 2-hydroxymethyl-pyrrolidin-1-yl.

4. A compound of claim 1 wherein Q is selected from the group consisting of phenyl, 2-chloro phenyl, 3-chloro phenyl, 3-bromophenyl, 3-(trifluoromethyl) phenyl, 4-chloro phenyl, 4-bromo phenyl, 4-iodo phenyl, 4-(trifluoromethyl) phenyl, 4-nitrophenyl, 4-methoxy phenyl, 4-(difluoromethoxy) phenyl, 4-(trifluoromethoxy) phenyl, 3-bromo 4-(difluoromethoxy) phenyl, 4-(2,2-dibromo ethenyl) phenyl, 4-ethynyl phenyl, 4-benzyl phenyl, 3,4-dibromo phenyl, 2,4-dichlorophenyl, 3,4-dichloro phenyl, 3,4-difluorophenyl, 3-chloro 4-iodo phenyl, 4-bromo 3-chloro phenyl, 4-bromo 2-fluoro phenyl, 4-bromo 3-fluoro phenyl, 4-bromo 3-(trifluoromethyl) phenyl, 4-chloro 3-(trifluoromethyl) phenyl, 3,5-bis (trifluoromethyl) phenyl, 3,4,5-trichloro phenyl, 4-bromo 3,5-dichloro phenyl, 3-phenoxyphenyl, 4-(fluoro 3-phenoxy) phenyl, 3-bromo 4-(trifluoromethylsulphonyloxy) phenyl, 3,4-bis (trifluoromethylsulphonyloxy) phenyl, 2-naphthyl or 5-bromo 2-naphthyl and 6-bromo 1-napthyl.

5. A compound of claim 1, in which the steric configuration of Q₁ is such that the Q—(CH₂)$_a$—(X₁)$_b$— group is in trans position relative to the Q₂—C(X₂)—N(R₁)(R₂) group.

6. Compound of formula (I) as defined in any one of claims 1 to 5, in which Q₁ is non-substituted or substituted by 1 or 2 halogen atoms or 1 or 2 methyl radicals.

7. A compound of claim 1 wherein Q₁ is selected from the group consisting of 1,2-cyclopropanediyl, 1-fluoro 1,2-cyclopropanediyl, 1-chloro 1,2-cyclopropanediyl, 1-bromo 1,2-cyclopropanediyl, 1-methyl 1,2-cyclopropanediyl, 3,3-dibromo 1,2-cyclopropanediyl and 1,2-difluoro 1,2-cyclopropanediyl.

8. A compound of claim 1 wherein Q₂ is selected from the group consisting of ortho-phenylene, meta-phenylene, paraphenylene, 1,2-naphthylene, 1,3-naphthylene, 1,4-naphthylene, 1,5-naphthylene, 2,5-naphthylene, 4,5-indenylene, 4,6-indenylene, 4,7-indenylene, 4,5-indanylene, 4,6-indanylene, 4,7-indanylene, 1,2,3,4-tetrahydro 5,6-naphthylene, 1,2,3,4-tetrahydro 5,7-naphthylene, 1,2,3,4-tetrahydro 5,8 -naphthylene, non substituted or substituted by 1 to 4 substituants.

9. A compound of claim 8 wherein Q₂ is selected from the group consisting of 2-methyl-1,4-phenylene, 2,3,5,6-tetrafluoro 1,4-phenylene, 3-methyl 1,4-phenylene, 2-chloro 1,4-phenylene, 2-acetylamino 5-chloro 1,4-phenylene, 2-amino 5-chloro 1,4-phenylene, 2-dimethylamino 5-chloro 1,4-phenylene.

10. A compound of claim 1 which is cis 4-[2-(3,4-dibromo-phenyl)-1-fluorocyclopropyl]-N-(1,4-oxazin-4-yl)-benzamide.

11. A method of combatting pests in rice and cotton crops comprising applying to said crops a pesticidally effective amount of a compound of claim 1.

12. A method of combatting insects comprising contacting insects with an insecticidally effective amount of a compound of claim 1.

13. The method of claim 12 wherein the compound is cis 4-[2-(3,4-dibromo-phenyl)-1-fluorophenyl)-N-(1,4-oxazin-4-yl)-benzamide.

* * * * *